United States Patent
Schwarz

(10) Patent No.: US 11,141,219 B1
(45) Date of Patent: Oct. 12, 2021

(54) SELF-OPERATING BELT

(71) Applicant: BTL Healthcare Technologies, a.s., Prague (CZ)

(72) Inventor: Tomáš Schwarz, Prague (CZ)

(73) Assignee: BTL Healthcare Technologies, a.s., Prague (CZ)

( * ) Notice: Subject to any disclaimer, the term of this patent is extended or adjusted under 35 U.S.C. 154(b) by 227 days.

(21) Appl. No.: 15/678,915

(22) Filed: Aug. 16, 2017

Related U.S. Application Data

(60) Provisional application No. 62/375,796, filed on Aug. 16, 2016.

(51) Int. Cl.
| | |
|---|---|
| *A61N 5/00* | (2006.01) |
| *A61F 7/08* | (2006.01) |
| *A61B 18/18* | (2006.01) |
| *A61F 13/64* | (2006.01) |

(Continued)

(52) U.S. Cl.
CPC .............. *A61B 18/18* (2013.01); *A61F 13/64* (2013.01); *A61F 13/66* (2013.01); *A61B 2018/00005* (2013.01); *A61B 2018/00172* (2013.01); *A61B 2018/00273* (2013.01); *A61B 2018/00464* (2013.01); *A61B 2018/00654* (2013.01); *A61B 2018/00916* (2013.01);

(Continued)

(58) Field of Classification Search
CPC .......... A61B 18/18; A61B 2018/00988; A61B 2018/00273; A61B 2018/00172; A61B 2018/00958; A61B 2018/00994; A61B 2018/00916; A61B 2018/00464; A61B 2018/00005; A61B 2018/00654; A61F 13/64; A61F 13/66
See application file for complete search history.

(56) References Cited

U.S. PATENT DOCUMENTS

| | | | |
|---|---|---|---|
| 5,419,344 | A | 5/1995 | Dewitt |
| 5,755,753 | A | 5/1998 | Knowlton |
| 5,919,219 | A | 7/1999 | Knowlton |

(Continued)

FOREIGN PATENT DOCUMENTS

| | | |
|---|---|---|
| BR | PI08125023 | 6/2015 |
| CN | 102711706 | 10/2012 |

(Continued)

OTHER PUBLICATIONS

Maximus Non-invasive Body Shaping System User Manual, http://download.lifvation.com/Maximus_UserManual.pdf, May 2012 (44 pages).

(Continued)

*Primary Examiner* — Mark W. Bockelman
(74) *Attorney, Agent, or Firm* — Riverside Law LLP

(57) ABSTRACT

A method of treating tissue of a patient uses a device including a mother case, a belt, at least one treatment unit and at least two applicators. The treatment method may include attaching first and second applicators to the belt at a working distance to the patient's surface, and providing different treatment energy to the first applicator and the second applicator. A treatment pattern is created by the applicators providing the different treatment energies. The hardware pattern or positions of the applicators on the belt may be changed before and/or during the treatment. The hardware pattern may be based on selected treatment effect and body part.

30 Claims, 14 Drawing Sheets

(51) Int. Cl.
*A61F 13/66* (2006.01)
*A61B 18/00* (2006.01)

(52) U.S. Cl.
CPC ........... *A61B 2018/00958* (2013.01); *A61B 2018/00988* (2013.01); *A61B 2018/00994* (2013.01)

(56) References Cited

U.S. PATENT DOCUMENTS

| | | | |
|---|---|---|---|
| 6,094,599 | A | 7/2000 | Bingham |
| 6,246,905 | B1* | 6/2001 | Mogul ................ A61B 50/10 607/3 |
| 6,273,884 | B1 | 8/2001 | Altshuler |
| 6,311,090 | B1 | 10/2001 | Knowlton |
| 6,453,202 | B1 | 9/2002 | Knowlton |
| 6,735,481 | B1 | 5/2004 | Bingham |
| 6,920,883 | B2 | 7/2005 | Bessette |
| 7,083,580 | B2 | 8/2006 | Bernabei |
| 7,376,460 | B2 | 5/2008 | Bernabei |
| 7,496,401 | B2 | 2/2009 | Bernabei |
| 7,520,875 | B2 | 4/2009 | Bernabei |
| 7,532,926 | B2 | 5/2009 | Bernabei |
| 7,571,003 | B2 | 8/2009 | Pozzato |
| 7,618,429 | B2 | 11/2009 | Mulholland |
| 7,914,469 | B2 | 3/2011 | Torbati |
| 7,945,321 | B2 | 5/2011 | Bernabei |
| 7,953,500 | B2 | 5/2011 | Bingham |
| 8,172,835 | B2 | 5/2012 | Leyh |
| 8,454,591 | B2 | 6/2013 | Leyh |
| 8,457,751 | B2 | 6/2013 | Pozzato |
| 8,548,599 | B2 | 10/2013 | Zarsky |
| 8,646,239 | B2 | 2/2014 | Rulon |
| 8,700,176 | B2 | 4/2014 | Azar |
| 8,725,270 | B2 | 5/2014 | Towe |
| 9,061,128 | B2 | 6/2015 | Hall |
| 9,168,096 | B2 | 10/2015 | Kreindel |
| 9,265,690 | B2 | 2/2016 | Kriksunov |
| 9,532,832 | B2 | 1/2017 | Ron Edoute |
| 9,561,357 | B2 | 2/2017 | Hall |
| 9,596,920 | B2 | 3/2017 | Shalev |
| 9,782,324 | B2 | 10/2017 | Crunick |
| 9,867,996 | B2 | 1/2018 | Zarsky |
| 10,195,453 | B2 | 2/2019 | Schwarz |
| 10,583,287 | B2 | 3/2020 | Schwarz |
| 2002/0165590 | A1 | 11/2002 | Crowe |
| 2003/0149451 | A1 | 8/2003 | Chomenky |
| 2004/0093042 | A1 | 5/2004 | Altshuler |
| 2004/0162583 | A1 | 8/2004 | Bingham |
| 2004/0230226 | A1 | 11/2004 | Bingham |
| 2006/0206103 | A1 | 9/2006 | Altshuler |
| 2006/0271028 | A1 | 11/2006 | Altshuler |
| 2007/0293911 | A1 | 12/2007 | Crowe |
| 2009/0043293 | A1 | 2/2009 | Pankratov |
| 2009/0326571 | A1 | 12/2009 | Mulholland |
| 2010/0004536 | A1 | 1/2010 | Rosenberg |
| 2010/0004715 | A1 | 1/2010 | Fahey |
| 2010/0016761 | A1 | 1/2010 | Rosenberg |
| 2010/0274329 | A1 | 10/2010 | Bradley |
| 2011/0009737 | A1 | 1/2011 | Manstein |
| 2011/0046523 | A1 | 2/2011 | Altshuler |
| 2011/0172752 | A1 | 7/2011 | Bingham |
| 2012/0046653 | A1 | 2/2012 | Welches |
| 2012/0116271 | A1 | 5/2012 | Caruso |
| 2012/0271206 | A1 | 10/2012 | Shalev |
| 2012/0310311 | A1* | 12/2012 | Elkah ................ A61F 5/0009 607/102 |
| 2013/0123629 | A1 | 5/2013 | Rosenberg |
| 2013/0123764 | A1 | 5/2013 | Zarsky |
| 2013/0123765 | A1 | 5/2013 | Zarsky |
| 2013/0158634 | A1 | 6/2013 | Ron Edoute |
| 2013/0238061 | A1 | 9/2013 | Ron Edoute |
| 2014/0249609 | A1 | 9/2014 | Zarsky |
| 2014/0276248 | A1* | 9/2014 | Hall ................ A61N 1/0432 601/2 |
| 2015/0157873 | A1* | 6/2015 | Sokolowski ......... A61N 2/02 600/14 |
| 2016/0045755 | A1 | 2/2016 | Chun |
| 2016/0106982 | A1 | 4/2016 | Cakmak |
| 2016/0121112 | A1 | 5/2016 | Azar |
| 2016/0158574 | A1 | 6/2016 | Eckhouse |
| 2017/0050019 | A1 | 2/2017 | Ron Edoute |
| 2017/0100585 | A1 | 4/2017 | Hall |
| 2017/0143958 | A1 | 5/2017 | Shalev |
| 2017/0239467 | A1 | 8/2017 | Shalev |
| 2019/0000529 | A1 | 1/2019 | Kothare |
| 2019/0134414 | A1 | 5/2019 | Prouza |
| 2019/0151655 | A1 | 5/2019 | Hall |
| 2019/0192219 | A1 | 6/2019 | Kreindel |
| 2019/0314629 | A1 | 10/2019 | Kreindel |
| 2019/0314638 | A1 | 10/2019 | Kreindel |
| 2019/0350646 | A1 | 11/2019 | Kreindel |
| 2020/0129759 | A1 | 4/2020 | Schwarz |
| 2020/0237424 | A1 | 7/2020 | Hunziker |
| 2020/0281642 | A1 | 9/2020 | Kreindel |

FOREIGN PATENT DOCUMENTS

| | | |
|---|---|---|
| EP | 2461765 | 6/2012 |
| EP | 2501352 | 9/2012 |
| EP | 2614807 | 7/2013 |
| EP | 3389532 | 10/2018 |
| JP | 2013063285 | 4/2013 |
| KR | 20120037011 | 4/2012 |
| KR | 20130128391 | 11/2013 |
| KR | 101941863 | 1/2019 |
| WO | 0112089 | 2/2001 |
| WO | 2004108211 | 12/2004 |
| WO | 2008012827 | 1/2008 |
| WO | 2009013729 | 1/2009 |
| WO | 2009044400 | 4/2009 |
| WO | 2011016019 | 2/2011 |
| WO | 2011058565 A2 | 5/2011 |
| WO | 2011156495 | 12/2011 |
| WO | 2012029065 | 3/2012 |
| WO | 2013074576 | 5/2013 |
| WO | 2014141229 | 9/2014 |
| WO | 2014149021 | 9/2014 |
| WO | 2014151431 | 9/2014 |
| WO | 2017103923 A1 | 6/2017 |
| WO | 2020002801 | 1/2020 |
| WO | 2020035852 | 2/2020 |

OTHER PUBLICATIONS

Trifractional FAQs, http://pollogen.lifvation.com/FAQ/TriFractional%20FAQs.pdf, Aug. 2011 (4 pages).
TriLipo MED Procedure, http://download.lifvation.com/Maximus_TriLipoMED_Intro.pdf, Apr. 2013 (66 pages).
Venus Swan, http://www.medicom.cz/UserFiles/File/LekarskeNenue/020Swan%20EN.pdf, Apr. 2016 (2 pages).
Kobach et al., A Simulation Approach to Optimizing Performance of Equipment for Thermostimulation of Muscle Tissue using COMSOL Multiphysics, Biophysics & Bioeng. Letters, 4(2), (2011) (26 pages).
Mekawy et al., Influence of Electro-lipolysis on Lipid Profile and Central Obesity in Obese Premenopausal Women, Bull. Fac. Ph. Th. Cairo Univ., vol. 17, No. 1 Jan. 2012 pp. 59-68.
Wanitphakdeedecha et al., Treatment of abdominal cellulite and circumference reduction with radiofrequency and dynamic muscle activation, J. Cosmetic and Laser Therapy, 17:5, 246-251 (2015).

* cited by examiner

SELF-OPERATING BELT

FIELD OF THE INVENTION

The field of the invention is an apparatus and methods with a high degree of modularity directed to a self-operated device for aesthetic treatment using a combination of one or more treatment applicators that may provide one or more types of treatment energy to the patient's tissue.

BACKGROUND OF THE INVENTION

Human skin is tissue which is commonly treated in order to improve its visual appearance. Skin is composed of three basic elements: the epidermis, the dermis and the hypodermis or so called subcutis. The outer and also thinnest layer of skin is the epidermis. The epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of fat cells. Fat cells create lobules which are bounded by connective tissue, fibrous septa (retinaculum cutis).

Another part of adipose tissue located in the peritoneal cavity is known as abdominal obesity. The visceral fat layer forming visceral white adipose tissue (VWAT) is located between the parietal peritoneum and the visceral peritoneum, closely below muscle fibers adjoining the hypodermis layer.

Excess adipose tissue in the subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been linked to various cardiovascular diseases and diabetes.

Undesirable skin appearance (e.g. topographic skin appearance) may also be caused by changes in the dermal or sub-dermal layer of the skin, especially by excessive quantity or volume of fat cells, weakening of fibrous septas, loss of elasticity, collagen structural or volume changes and/or limited lymph flow, which may result in the accumulation of toxins.

Pigment inhomogeneity caused by structural changes in the epidermis, by pigment granules contraction, expansion, or pigment migration in the skin may also lead to low self-confidence in people with this skin condition.

Current devices for aesthetic use have limited modularity. An operator may have to use two or more different applicators and provide separate treatments one at a time in order to achieve the most desirable results. This is time consuming and expensive and therefore some patients may not be able to afford it. No device and/or method in the current state of art is able to provide large scale of treatment therapies during one treatment session, with a large treatment area and large range of hardware modularity. Current state of art systems are not able to change hardware patterns during one session, cannot connect to another device during treatment and cannot operate without an operator. No device of the current state of art can resist obsolescence like the presented modular device and method of use. Self-operated devices have several benefits e.g.: fast reaction under changing therapy conditions, preventing human mistakes, time saving, saving data from previous treatments and learning from them etc. Multiple therapies also improve the effect and safety of the treatment. Operator guided treatment applicators are not able to simultaneously provide multiple different therapies across the large patient surface. There is a need for apparatus and methods that allow an operator to choose several treatment types that can treat with minimal intervention by the user.

Current state of art apparatuses providing complex treatments are very expensive, which results in high prices for treatment sessions. The price of current state of art apparatuses may be also the reason why a purchaser hesitates when choosing between a cheap lower quality apparatus and an apparatus of high quality, which is very expensive.

One solution for reducing the initial cost of high quality apparatuses may be renting a device adapted to these needs.

SUMMARY OF THE INVENTION

Described herein is a device and method of its use for aesthetic treatment with multiple types of treatment energy that may be delivered into various body parts including e.g.: bra fat area, buttocks, saddlebags, love handles, abdomen, hips, thighs, arms, limb, back, cervical body part, also a muscle or muscle group of the mentioned body parts and/or any other tissue. Treatment energy may be delivered to the tissue of the patient in a sequential and/or simultaneous manner. Different aesthetic skin and/or body treatment effect are provided, e.g.: wrinkle reduction, skin tightening, skin rejuvenation, skin viability, removing of unwanted hair, removing of pigment and/or other skin imperfections (e.g.: atopic eczema, psoriasis, erysipelas, dermatomyositis, lupus, hives, acne, skin veins and/or scars, collagen inhomogeneity, etc.), removing of cellulite, body shaping, muscle stimulation, fat removing, anti-edema and anti-erythema effect, improving blood and lymph circulation, and/or accelerating body metabolism.

In one aspect the device is designed as a mother case with one or more treatment units ensuring control and/or generation of treatment energy, one or more applicators directing the treatment energy into the body and a belt for positioning the applicators into a pattern in proximity to the patient's body. The mother case may be modularly modified by adding and/or removing one or more parts of the device (e.g.: applicators, treatment units) before and/or during the treatment.

Treatment applicators may provide different types of treatment energy e.g.: radio-frequency therapy (RF therapy), plasma therapy, ultra-sound therapy, acoustic wave, shock wave therapy, light (coherent, non-coherent) therapy, heating, cooling, electro-therapy, therapy by generated magnetic field (including muscle stimulation), positive or negative pressure therapy, vibration therapy and/or massage therapy. Treatments may be performed completely without manual operation or even attendance of the operator and/or treatment procedures may by modified during the treatment. One or more treatment applicators may communicate with each other and/or with one or more control units via cables, wireless and/or via a connection through the belt. The communication may provide information about the location and/or type of the applicator, treatment protocol, treatment parameters and other information.

The invention is characterized by a method and modular apparatus with a belt and/or arrangement of applicators enabling multiple treatment procedures and/or therapies at the same time. This improves the effectiveness of the treatment and/or reduces the time needed for the treatment and improves homogeneity and safety. The combination also provides treatments for the same or different tissue structures which may result in synergistic improvement of treatment results.

The belt is designed to fit any type and size of treated patient body area. In one preferred embodiment the belt is created by a supporting matrix with attached applicators in an arbitrary 2D or 3D hardware pattern. The belt is in touch with the patient's body surface and matches the curvature of the patient's body. The belt is designed in order to fit one or more applicators providing at least two different types of treatment energy. The size of the belt may be variable by stretching and/or by plugging and/or removing of one or more parts of the supporting matrix part and/or applicators. The supporting matrix enables placement of the applicator at a working distance at an arbitrary location on the patient's body.

In another embodiment the belt may be considered as a block of at least two treatment applicators attached at an optimal working distance to the patient's body.

The modular apparatus may operate without any manual operation or even without and/or with slight attendance of an operator, which saves time and money. One operator may supervise more than one treated patient. The apparatus may prevent mistakes during treatment caused by human factors. The apparatus may also have a better response to changed treatment conditions and/or may provide more homogenous and precise treatment which improves results and safety of the treatment. With the apparatus controlled by a computer, responses to changed conditions are improved because the apparatus can react on e.g.: movement of the patient or structural changes in the soft tissue, etc.; faster than 0.1 seconds, where human response is at least 0.5 seconds.

The modular apparatus with a belt provides an easy way to change treatment procedures and parameters before and/or during the treatment. The modular system provides various patterns of treatment based on treatment applicators connected to the belt. The modular system may provide to the operator a suggestion of applicator displacement in the belt system based on treatment effect, age, sex and or other parameters. Such modularity enables personalized treatment for each patient.

The present invention solves the problem of device obsolescence due to large scale modularity. The device and method enable hardware and/or treatment pattern changes. The belt may or may not contain a supporting matrix. The belt may be flexible, whole or partly elastic and may be adapted to a patient surface of arbitrary size and shape. This characteristic helps to provide optimal energy transfer from an applicator to the patient soft tissue. Improved contact with the patient skin or surface may decrease or prevent an edge effect, backscattering of delivered energy and/or provides better conditions for collecting feedback information. The supporting matrix may also be connected to upper side of the applicator, may keep one or more applicators in touch with the patient surface, and may not be in touch with the patient.

In another embodiment the device may comprise several treatment units. Each treatment unit ensures control and/or generation of treatment energy for at least one treatment applicator. The separation of treatment units decreases the price of the device and a customer may add (purchase or rent) additional treatment units according to his needs and improve the functionality of the device. In an alternative embodiment the treatment units may be plugged into a mother case. Modularity may also protect the presented device against obsolescence.

One treatment unit may be specialized for providing particular treatment energies and particular treatment effects. In order to achieve the necessary scale of treatment effects another treatment unit may be specialized for providing different treatment energies and different treatment effects. The treatment units may include different components and/or different technological level of components which may allow only the therapies the operator needs.

In one embodiment the device may contain a master unit and one or more therapy generators.

In still another embodiment one or more of the applicators may include its own control unit which may cooperate with one or more control units of the respective treatment unit and/or with a central control unit. The device also may include billing and rental systems for renting of the device, treatment units and/or applicators and billing the user by the treatment procedure or length of rental. A customer may improve its use of the device by renting only the modules necessary for his needs, allowing for reductions in cost, improving accessibility to doctors and clinics.

In another embodiment the presented method and device may include emulator software and/or hardware parts that allow interconnecting arbitrary external devices, treatment units, or applicators in order to communicate and participate in the treatment pattern.

The device may include a communication system that enables communication between external devices e.g. PC, laptop, mobile and others.

According to one embodiment the belt may be wearable and the mother case with treatment unit/s may be part of the wearable belt.

GLOSSARY

Tissue includes skin, muscles, fat, fibrous tissue, nervous tissue (e.g. neurons, motor neuron, and neuromuscular junction), connective tissue, bone tissue and other human or animal tissue.

A patient is a biological material, mainly a human or an animal body.

DETAILED DESCRIPTION

Figure 1:
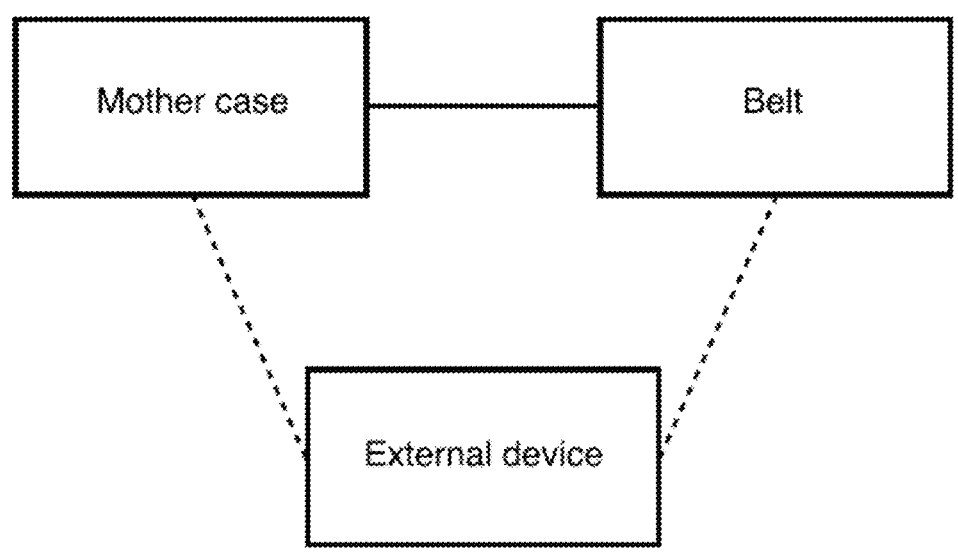
FIG. 1 is schematic diagram representing main segments of the device and communication between them.

FIG. 1 is a schematic diagram representing main segments of the device and communication between them. The device is designed as a mother case with one or more treatment units ensuring control and/or generation of treatment energy, and a belt with one or more applicators directing the treatment energy into the body. The belt displaces the applicators into the pattern in proximity of the patient's body. The mother case may be alternatively connected with an external device connected with the belt by its own separate applicator. According to another embodiment the mother case may be substituted by one or more treatment units and/or external device(s).

Figure 2:
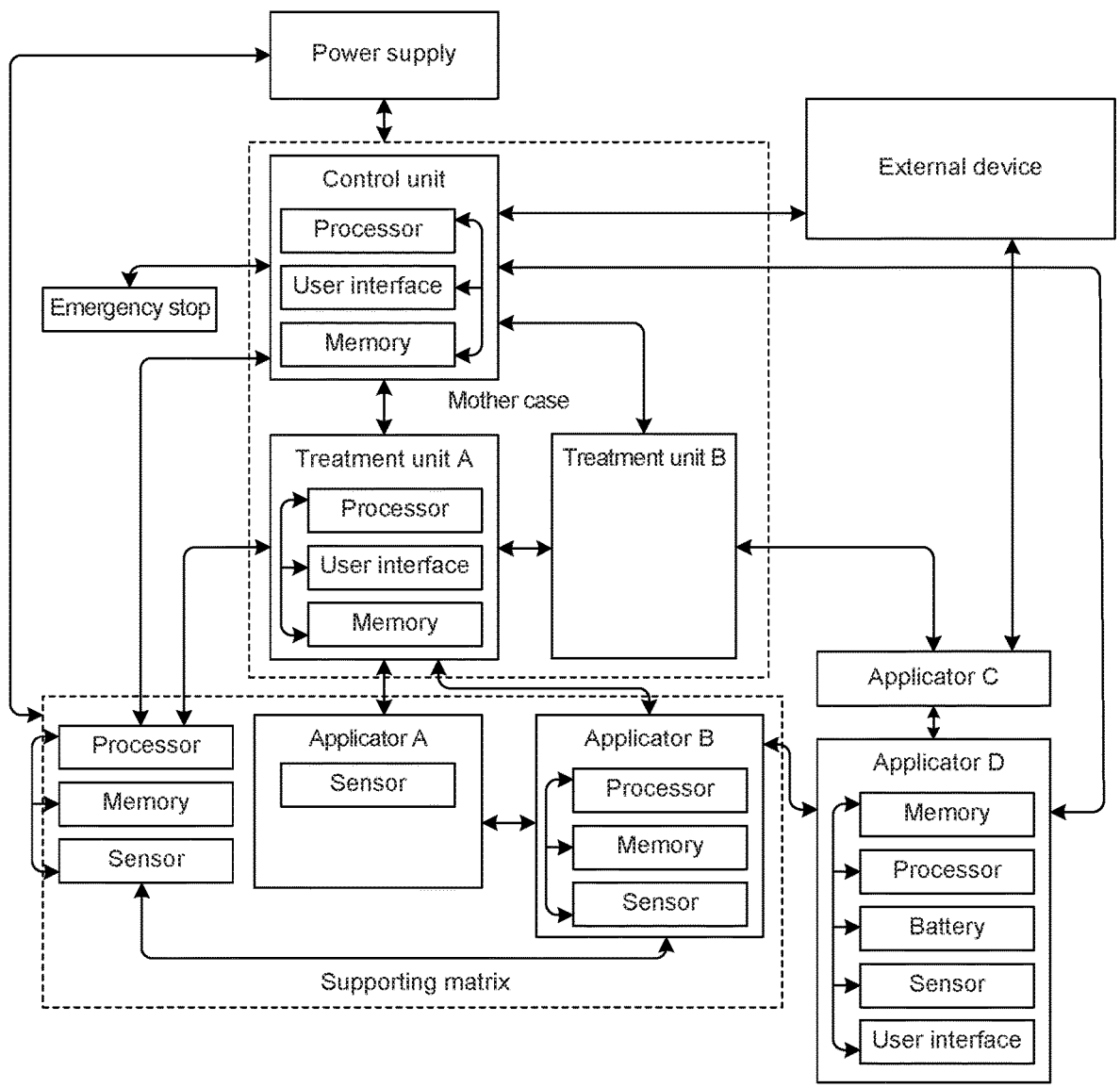
FIG. 2 is a schematic diagram of one possible embodiment of the device and communication between its individual parts.

FIG. 2 is a schematic diagram of one possible embodiment of the device and communication between its individual parts. The device is powered by a power supply. The power supply may be electricity from an external source e.g. electrical power grid; and/or from batteries included in any part of the device. Part of the device such as: a mother case, a control unit, a belt (e.g. supporting matrix), one or more treatment units, one or more external devices and/or one or more applicators may include a direct connection with the power supply and/or may include batteries. Any part of the device may be powered through a connection between other part(s) of the device. For example, the applicator may be powered by the treatment unit, by the supporting matrix, by the mother case and/or by another part of the device. Also one or more treatment units may be powered e.g. by the mother case, external device, supporting matrix and/or directly by connection to the power grid.

According to one of possible embodiment illustrated in FIG. 2, A supporting matrix may be powered by the power supply and then be used as power supply for several applicator(s) attached to the supporting matrix.

The mother case described in detail later in this document may include the control unit and/or one or more treatment units which may have different specifications. Treatment units and applicators may be specialized to provide specific type(s) of treatment therapies by one or more treatment energies and/or may cause one or more treatment effect(s). The control unit may process treatment parameters, protocols and/or other information based on binary code.

The treatment unit may include hardware and/or software components that may modify incoming electric signals and/or communication signals to the treatment unit. Such modified electric signals and/or communication signals may be provided into the applicator(s), supporting matrix, external device and/or another part of the device in order to provide treatment energy from one or more specific treatment energy sources. The applicator(s) may also modify the delivered electrical signal and/or process communication information.

As illustrated in the FIG. 2, some parts of the device e.g. treatment unit B, may not include a processor, a memory, a sensor, a battery, a user interface and/or other feature. The missing features may be substituted by other parts of the device including such features.

As illustrated in the FIG. 2, the device may include a processor and may process information individually and/or in cooperation with other parts including the processor. In one embodiment any processor may receive stored information from any memory of one or more parts of the device.

The belt may be designed as a supporting matrix with attached applicators at an optimal working distance from the patient's body. The optimal working distance may be different for different types of the applicators and/or different treatment energy sources. For example, the optimal working distance for a muscle stimulating electrode may be direct contact with the patient's surface. On the other hand, the optimal working distance for an RF electrode for heating of a patient's adipose tissue may be several millimeters. The optimal working distance of the applicator(s) and/or treatment energy source(s) may be set by the design of the applicator(s), a supporting matrix, a spacing object and/or a fastening member. The applicator(s) may be in contact with patient's surface and/or in proximity to patient's surface and separated from the patient's surface by any material and/or air gap.

According to another embodiment, the belt may consist of a hardware pattern of treatment energy sources where at least two of the energy sources provide different types of treatment energy. The hardware pattern of treatment energy sources may be predefined from the factory and/or, according to another embodiment, may be rearranged according to individual needs of the patient. The belt, according to said embodiment, may be wearable during the day, wherein the mother case (e.g frame with GUI) with treatment unit(s) may be incorporated inside the wearable belt. According to said embodiment, the patient may choose one of several predefined treatment protocols from a list of treatment protocols. Protocols may be based on one or more desired treatment effect(s), treated body part(s), the hardware pattern of the belt and/or other features. The belt according to such an embodiment may be remote controlled, by the patient and/or by any other educated competent user. The belt, according to said embodiment, may be wireless and may be powered by batteries. According to still the same embodiment the belt may be in wireless communication with an external device.

The support matrix may include a processor, memory and/or a sensor for monitoring and/or evaluating at least one treatment parameter and/or may send feedback information to any connected part of the device e.g.: the control unit, the treatment unit(s), the external device(s) and/or the applicator(s). Some of the applicators may not be attached to the supporting matrix but may communicate with the supporting matrix. Applicators may also communicate between each other.

Any part of the device may include a manual and/or a virtual emergency stop button. The emergency stop button may immediately stop any and/or all delivery of treatment energies to the patient's body.

Figure 3:
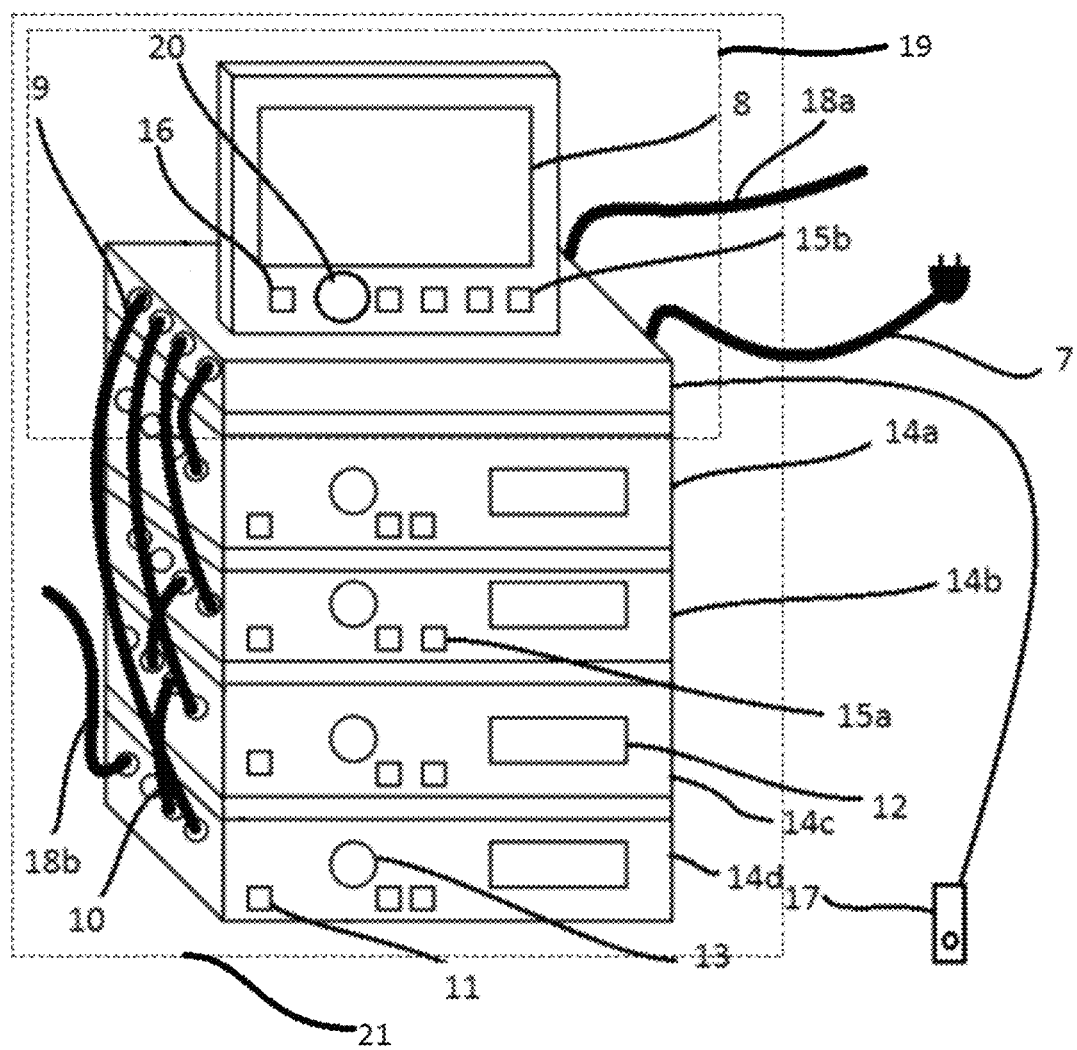
FIG. 3 illustrates a mother case with a control unit and multiple treatment units.

FIG. 3 depicts a mother case with a control unit and multiple treatment units. The mother case may include the control unit 19 of the mother case 21 and one or more treatment units (14a-14d) that may be added according to treatment needs. Individual treatment units (14a-14d) may be designed to provide one or more specific treatment effects and/or one or more treatment energies e.g. RF waves, an electrical current, a magnetic field, acoustic waves, a shock wave, ultrasound waves, light waves, applied lower/higher pressure, friction, plasma, heating, cooling and/or any other treatment energy. The control unit 19 may include a user interface in the form of a touch display 8, several buttons 15a, 15b, a circular control element 20, and a switch button 16. Also, each of the individual treatment units (14a-14d) may include its own user interface that may communicate with an external device, between other treatment units and/or with the control unit 19. The control unit 19 may include the processor and the memory in order to guide the treatment process, store information about treatment including feedback information consumption of individual parts of the device and/or may also include a billing system. The mother case 21, the control unit 19, the treatment units (14a-14d), and the external device or server may also include a black box (e.g. memory) for storing data of the treatment history, communication between individual parts of the device, data for a billing system and/or may store many other types of data.

The mother case 21 may include slots for the treatment units (14a-14d). The treatment unit may be fixed in the right position by a specific type of fastening mechanism that is described below. A fastening mechanism used to fix and/or connect treatment units (14a-14d) to the mother case 21 may by different for different types of treatment units (14a-14d) and/or may be universal for all of the treatment units (14a-14d)

Recognition of the treatment unit may be through the specific impedance of the connected part, an RFID tag, pins, a sequence of specific electrical and/or electromagnetic pulses, measuring of a magnetic field in/near the connection that may be specific for the individual type of the treatment unit, software recognition, a specific binary ID, by recognition of a connected optical signal from the treatment unit and/or through any other of one or more mechanisms. The described system for recognition of the treatment unit may also be used for recognition of individual applicator(s) and/or external device(s). Connection/communication between the mother case, treatment unit(s), the control unit, applicator(s), the supporting matrix and/or external device (s) may be performed wirelessly, by cable 9, by contact pins, by one or more magnets, by one or more conductive parts and/or by a chassis.

The treatment units (14a-14d) may guide treatment provided by one or more applicators independently of the control unit 19 or in cooperation with control unit 19. Some of the treatment units (14a-14d) may not include a processor, memory and/or a user interface and may be just means of connecting to one or more applicators and their management. The treatment units (14a-14d) may be also interconnected. The treatment units may be interconnected between each other.

The respective treatment units may be connected and fixed in the correct slot position of the mother case in a plug and play regime. The treatment unit may include an energy socket or pin connectors to be plugged into the mother case. At least one connector may ensure the energy charge, data communication and/or fluid communication (e.g. in case of cooling, or use of plasma) with the mother case. Alternatively, the data communication between mother case and treatment unit may be performed wirelessly, by cable, or one or more magnets. Recognition of the treatment unit may be through specific impedance, an RFID tag, pins, a sequence of specific electrical and/or electromagnetic pulses, measuring of a magnetic field that may be specific for the individual type of the treatment unit, software recognition and/or through any other of one or more mechanisms. The treatment unit may further include at least one socket/pin for the applicator. The treatment units and also the slots for the treatment units in the mother case may include electromagnetic shielding, vibration shielding, thermal shielding and electrical insulation. The plug and play modular device for individual connection of treatment units provides a large scale of modularity which decreases the cost for the device, requires less space for the device and increases versatility in order to fit all users.

Applicators directing the treatment energy into the body may be connected and/or communicate between each other, with the supporting matrix, with one or more treatment units, with the control unit 19 and/or with an external device. The applicator may include one or more of: treatment energy sources, processors, sensors and/or memory.

The external device may be used to provide and/or control at least part of the treatment. The external device may guide and/or communicate with at least one of: an applicator, a treatment unit and/or the control unit. The external device may be any treatment device able to provide a treatment energy source. The external device may be also be a device (e.g. computer, tablet, smartphone) that is not able to provide a treatment energy source but communicates with the device and is able to monitor treatment and/or adjust treatment parameters.

Communication between individual parts of the device may be based on peer-to-peer and/or master-slave communication. During peer-to-peer communication the individual parts of the device have the same priority of commands and communicate directly between each other. Peer-to-peer communication may be used during initial recognition of connected individual parts of the device. Peer-to-peer communication may be also used between some parts of the device during a treatment. Before and/or during each treatment master-slave communication is used at least for a short time.

During master-slave communication, one part of the device provides commands with highest priority. The part of the device that provides commands with the highest priority at that time is called the master unit.

According to one embodiment, a master unit may be determined by choice of a user before and/or during the treatment. The user may determine the master unit e.g.: the control unit, one of the treatment unit(s) or one or more external device(s) (e.g. laptop, tablet).

According to another embodiment the master unit may be determined automatically based on the predetermined priority value of connected parts of the device. For example, a treatment unit A may be the master unit but after connection of a treatment unit B or an external device to the mother case, the treatment unit B or the external device become the master unit.

At least two parts of the device and/or features may communicate with each other and/or with an external device by optical cable, conductive cable, by other conductive connection and/or wirelessly. Wireless communication may be provided by internet network, local network, RF waves, acoustic waves, optical waves, 3G, 4G, LTE networks, Bluetooth and/or any other.

FIG. 4-7 illustrates several possible master-slave communication schemes. According to the schemas in FIG. 4-7 a therapy generator generates a modified electrical signal in order to provide it to the treatment energy source and provide a treatment effect. Therapy generators may be e.g. a treatment unit, or one or more applicator(s).

The master unit according to the previous definition includes a processor and provides commands with highest priority.

Boxes labelled "Security" according to FIG. 4-7 may symbolize coding of the information used in communication and/or antivirus protection to prevent intrusion of unwanted binary code into the device and/or its communications. The security may also correct mistakes created during communications. The security may also the block connection of an unauthorized/unwanted external device to the device. According to FIG. 4 the security may be located in the communication diagram between the master unit and the communication interface. The security may also be part of a user, a service and/or a sale. According to another possible embodiment the security may be located also between the communication interface and a communication medium, between the master unit and a therapy generator and/or may be part of them.

The communication interface may include hardware and/or software. The communication interface allows transfer of communication signals between at least two different parts of the device or between one part of the device and the communication medium. The communication interface may translate the communication signal into readable form for both of the communicating sides. The communication interface may be e.g. a modem providing communication between the device and online network or server. According to some embodiments, the communication interface may be part of the master unit, the therapy generator, and/or other parts/features of the device.

The communication medium may be a medium for transferring communication data. The communication medium may be used in communication between the device and the user, the service and/or the sale. The communication medium may be e.g. wire, any conductive connection, server, some kind of network based on the principles of e.g.: RF waves, acoustic waves, optic waves, GSM, 3G, 4G, HUB switch, Bluetooth, Wi-Fi which may include one or more servers.

Communication data/information may be redirected to individual parts of the device and/or to individual end users like e.g. the user, the service and/or the sale; by the master unit, the communication medium, the therapy generator and/or individual end user(s). For example a server may filter select data for the user and filter other communication information that will be redirected to e.g. the server, control unit and/or other parts of the device.

Figure 4:
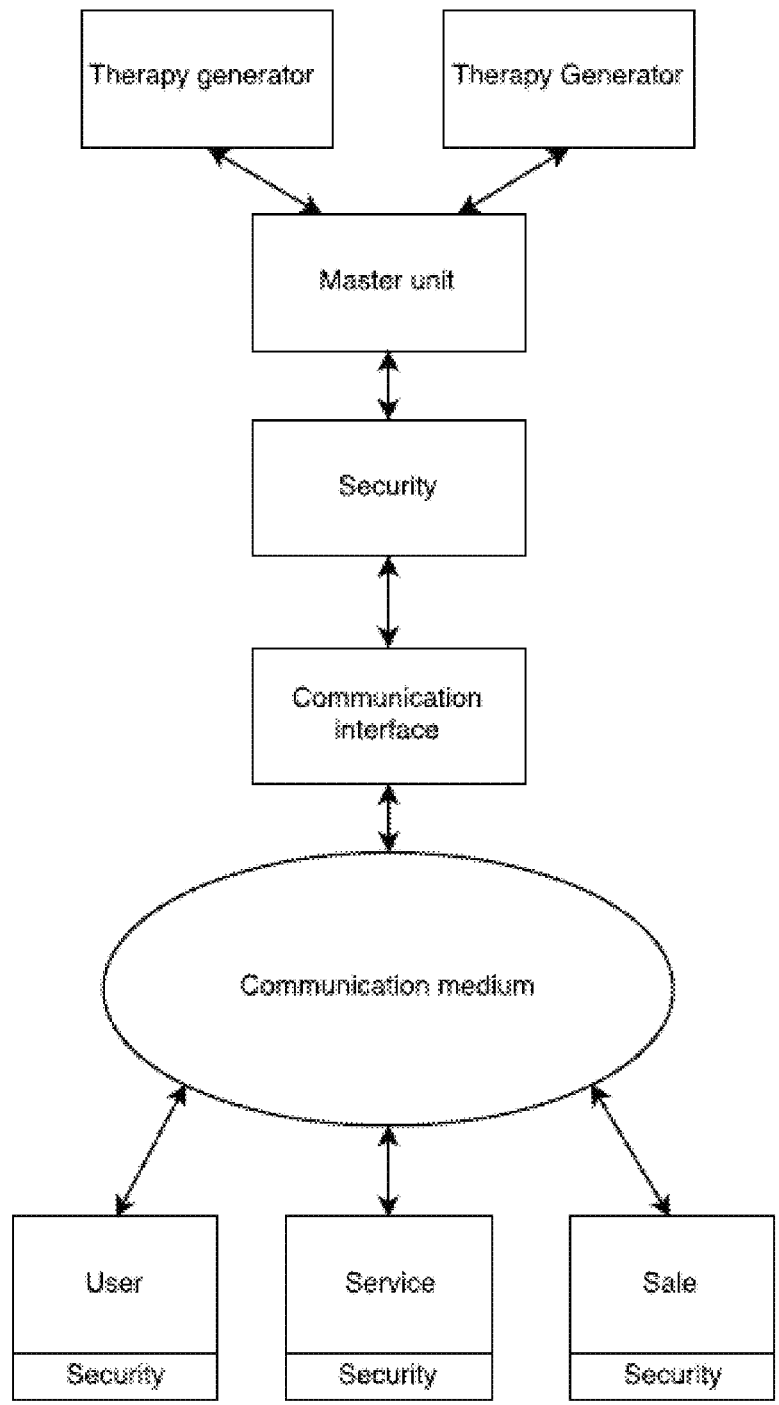
FIG. 4 is a schematic illustration of one possible communication between parts of the device and also external devices with remote access.
Figure 5:
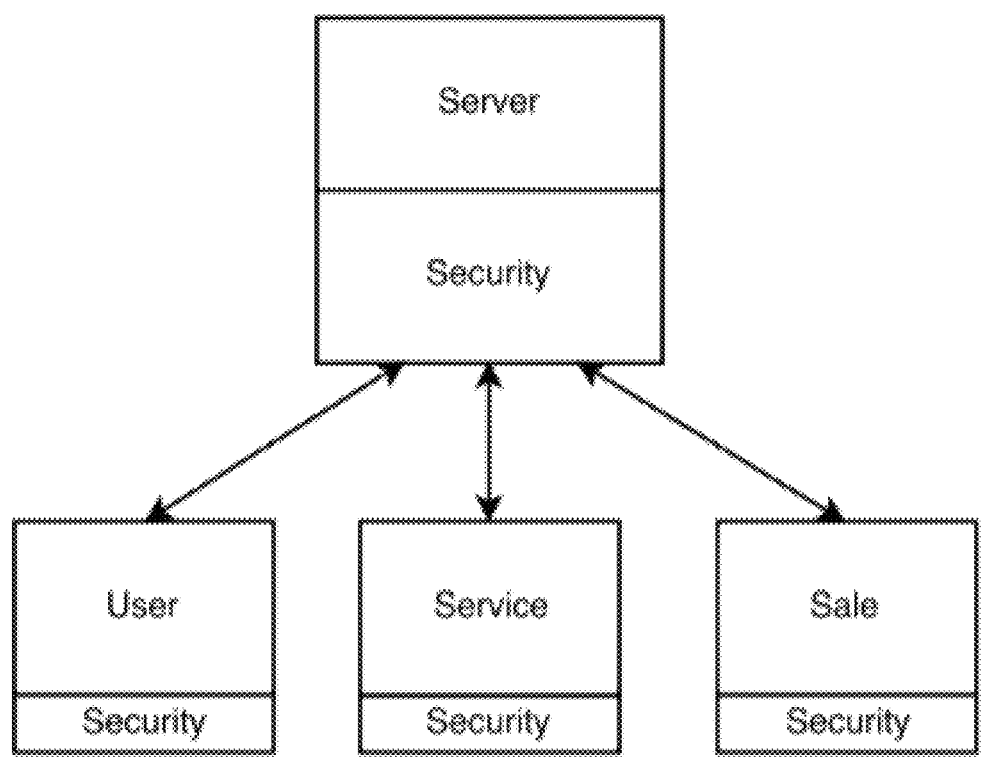
FIG. 5 is a schematic illustration of one possible communication diagram between server and part of the device.

According to FIG. 4-5, the box labelled "User" represents a user's communication device (laptop, mobile, tablet, etc.) that may send information to the device and/or receive information from the device. Information provided by this communication channel may be e.g. the type of treatment protocol, the treatment effect, treatment parameters, feedback information, the schedule of treatments, recommendations of behavior before and after the treatment and/or any other. Some of the user's information may be sent to the operator and some to the patient e.g. by an app device for mobile, tablet or laptop.

The app for a patient may be downloaded to any external device e.g. smartphone, tablet, computer and/or other. The app may communicate with the device and according to the protocol defined by user and/or provider of the device, the patient may display some of treatment protocol information e.g. progress of the treatment, the treated body part, the remaining time of the treatment, heart rate, temperature of the patient's body, provided type(s) of treatment energy, the desired treatment effect, and a comparison of patient's body parameters against previous treatment (like body fat percentage). The app for the patient(s) may inform about the schedule of treatments, recommendations of behavior before and after the treatment e.g. a drinking regimen, proposed exercises and their frequency and/or other.

According to FIG. 4 the box labelled "Service" represents a service department's communication device (laptop, mobile, tablet, etc.) that has authorized access to information about the device. The service department may be e.g. a service department of the device provider company. Information provided by this communication channel may be wear of the device and/or consumption of the device and its components, possible software optimization/actualization of the device, errors in the device, apps for connection of other external devices and/or other.

According to FIG. 4 the box labelled "Sale" represents a sales department's communication device (laptop, mobile, tablet, etc.) with authorized access to information about the device. Exchanged information may be e.g.: number of, time of and/or type of applied treatment. The sale department may send information about e.g.: the renting price of the device, billing for the treatment (described later as a billing system), special offers, the possibility of extending parts of the device, apps for the patients personal smart phones and/or other.

The device may also include a black box storing data of the treatment history, communications between individual parts of the device, and data for a billing system. The data may be accessible to the sale or to the service via the communication medium (e.g. a storage cloud and/or server). The system may manage charges for using the device or respective modules of treatment units and provide this information to the provider in order to prepare the invoice for renting.

The data from the black box may be downloaded only by a verified authorized person e.g. service technician, accountant. Verification of the authorized person may be e.g.: by a specific key, by a password, by a software code of several bits and/or by a specific interconnecting cable.

According to another embodiment the billing system may be based on credit subtracting from the user account. A user's credit may be predefined by the provider of the device e.g. the producer of the device; and/or may be recharged during the time of use. Credits may be subtracted according to the chosen treatment protocol. The credit value for treatment selected by the user may be displayed to the user before treatment starts, during the treatment and/or after the treatment. If the credits in the user account run out the device may not enable any further treatment until credit is recharged. As it is illustrated on the FIG. 4 communication between individual boxes may be bidirectional. According to FIG. 4 secured access of User, Service, and/or Sale may be used to input and/or receive information. Such information may be transferred and/or may be also processed through a Communication medium (e.g. in the server) and/or communication interface and/or master unit where each piece of information is sorted and a decision is made as to where it should be transferred or stored.

The connection between the User, Service, Sale and Communication medium and/or connection between the Therapy generator and Master unit may be secured by Security to provide safe communication and eliminate errors. Security may be also implemented between the Master unit and the Communication interface and/or between the Communication medium and the Communication interface.

Another possible communication between the User, the Service and/or the Sale to the device may be provided by a server (communication medium) illustrated in FIG. 5. The server may have implemented security. The security may or may not be also implemented upon individual access of the User, Service and/or Sale.

Figure 6:
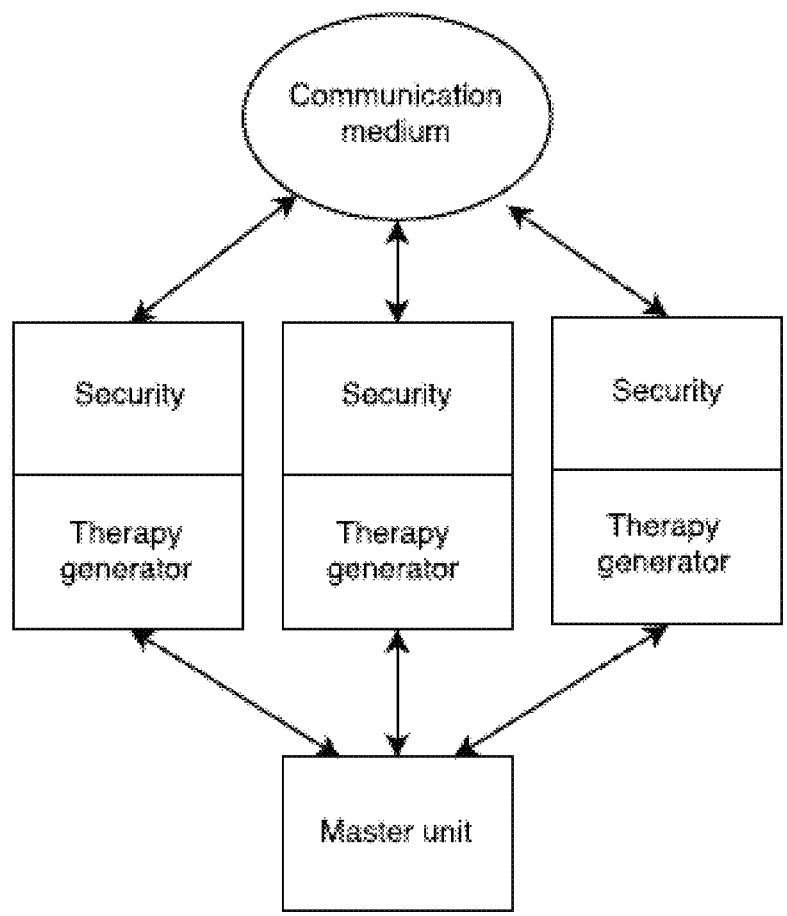
FIG. 6 illustrates communication between a communication medium, therapy generator and master unit.
Figure 7:
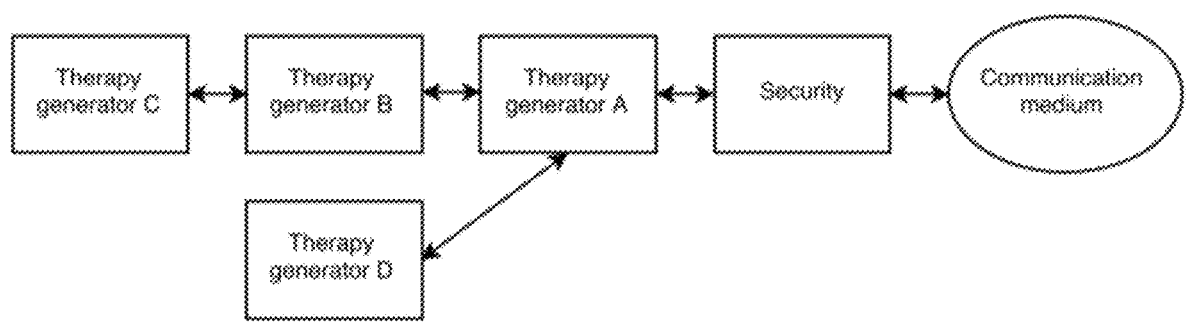
FIG. 7 is schematic diagram of serial communication between a communication medium and a therapy generator.

According to another embodiment depicted in FIG. 6 the communication medium may communicate with Therapy generator(s) and Therapy generator(s) may communicate with the Master unit. According to said embodiment communication information from the communication medium may be verified by the security before the therapy generator sends communication information to the master unit. FIG. 7 is schematic diagram of serial communication between a communication medium and therapy generators. The therapy generator A may communicate with at least one more therapy generator. Subsequent therapy generator B may also communicate with one or more therapy generator(s) e.g. a therapy generator C that does not directly communicate with the therapy generator A.

The device includes one or more applicators for directing the treatment energy into the body and a belt for positioning the applicators into a hardware pattern in proximity to the patient's body. Each applicator may provide one or more different type of treatment energy and/or treatment effect mentioned above and may also include a mechanism for cooling and/or heating of the patient surface and/or any part of the device. For example any applicator may cool itself and/or also part of the supporting matrix. Heating and/or cooling of the patient surface may create thermal gradient across the tissue. Controlled cooling and/or heating may create a volume with the highest/lowest temperature on the surface of the patient or may create a volume with the highest/lowest temperature located under the surface of the patient.

The applicator may include one or more sensors providing feedback information processed by processor and/or external device.

The applicators may have different sizes and shapes. Some of the applicators may have several square millimeters of active surface. The active surface is the side of the applicator oriented to the patient's surface and it is the part of the applicator which directs the treatment energy into the patient's body. The active surface of the applicator may be more than 10, 40, 50, 100, 200, 300, 500 square centimeters.

Applicators may have different shapes. Some of them may have an active surface with a symmetrical shape (e.g.: square, circular, elliptical, triangular, teardrop, rectangular, spidery and/or other types) and some of them may have an asymmetrical shape of the active surface.

The curvature of the active surface of the applicator may be different than the curvature of other parts of the applicator. The active surface of the applicator may have a regular curvature (e.g.: convex, concave, flat, partially elliptical etc.) and/or irregular curvature (e.g.: partly spherical, pointy, wavy, with some ridges etc.). The curvature of the active surface may also be a composition of several different curvatures. The active surface of the applicator may have at some area of active surface a different curvature than the curvature at another specific area of the same applicator. The curvature may create a specific shape on the active surface of the applicator. Some types of applicator's curvature may improve contact with the patient surface, may modify the provided treatment energy delivered to the patient, may increase the treatment comfort, may increase treatment efficiency e.g. (a design providing massage of the patient's surface) and/or may improve collecting of feedback information (e.g. a protruding sensor). The curvature of the active surface may also set the working distance of the applicator and/or may enable air (and/or liquid) to flow under the applicator. In some embodiments the applicator curvature across its active surface may be changeable during the time and/or a curvature may be used in order to provide massage of the patient.

Massage of the patient's soft tissue may be also provided by e.g.: a suction mechanism that creates different air pressure above the patient skin, by mechanical pressure of at least one massage element, massage by switching between parts of the device that creates mechanical pressure, massage by stimulation of neuromuscular plaque and/or muscle fibers, and massage by acoustic waves and/or ultrasound waves. In order to provide a patient's massage and/or other treatment effect the design of the applicator's active surface may be adapted to the specific treatment energy source.

According to a preferred treatment pattern massage may be provided in order to stimulate lymph and/or blood flow in the direction toward the lymph node and/or in the direction toward the heart.

A massage element is a part of the device that creates mechanical pressure on the patient's surface e.g. a protrusion on the applicator's active surface that may be movable.

The active surface of the applicator may be designed from material that is able to adapt to any curvature of the body (e.g.: memory foam, an elastic active surface of the applicator, and/or any other material).

The active surface of the applicator may be modified. Such modification of applicator's active surface may be provided by interchangeable attachments and/or by different exchangeable types of spacing objects located between patient's body and applicator's active. Modification of the applicator's active surface may be provided before, during and/or after treatment. A spacing object may be also part of the supporting matrix.

The active surface of the applicator may also contain one or more apertures of different sizes and shapes. The size and shape of one or more apertures may by variable during the time of the treatment. The apertures may be used to e.g.: provide air and/or liquid flow, may cool/heat patient's surface, and/or supply active substances as it is described in U.S. Provisional Application No. 62/331,060 incorporated herein by reference.

Also, the sizes and shapes of individual treatment energy sources may be variable e.g. RF electrodes as a source of RF treatment energy may have a variable surface as it is described in U.S. patent application Ser. No. 15/584,747 incorporated herein by reference.

One or more electrodes may have different sizes and shapes that influence the size of the treated area, the focus of the treatment, parameters of provided treatment energy and/or homogeneity of the treatment. Electrodes may be formed by conductive wire or a system of wires, by a conductive plate and/or other conductive or semi-conductive object. Shapes of electrodes may be asymmetrical or at least partially symmetrical e.g.: oval, elliptical, planar, square, wavy, convex, concave, spiral and/or other shape of electrode and/or shape of electrode surface. The electrode may consist of one or more pieces. An electrode with rounded edge(s) may minimize edge effects and prevent creation of hot spots. According to a preferred embodiment an RF electrode has a circular contour in a longitudinal cross section and at least partly elliptical shape of a lower part of the electrode 402a in vertical cross section, as shown in FIG. 16.

Figure 16:
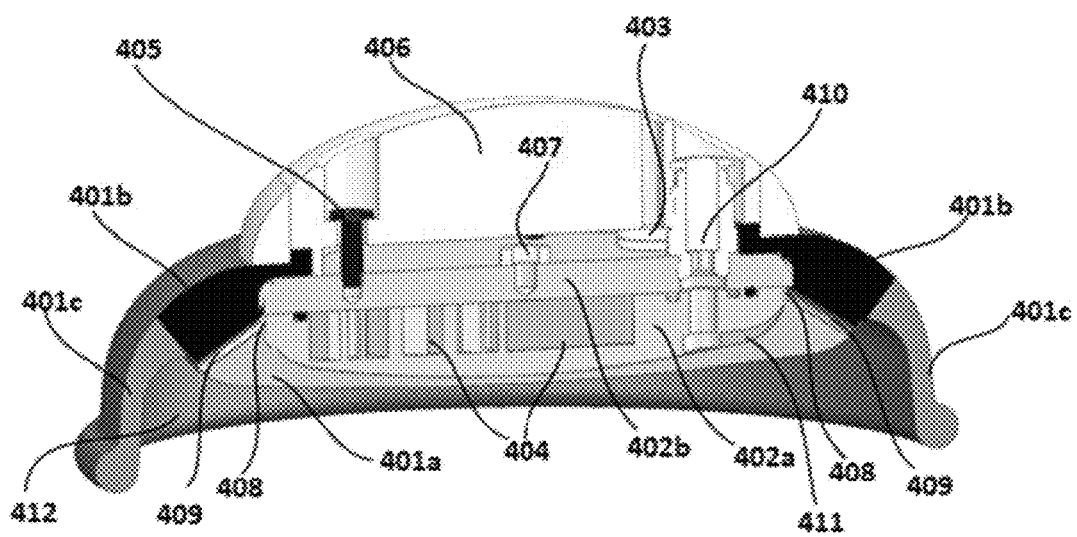
FIG. 16 illustrates an applicator embodiment.

A diameter of the RF electrode in FIG. 16 may be in the range from 0.6 cm to 40 cm or from 6 cm to 30 cm or from 6 cm to 15 cm or may have any other diameter.

The RF electrode of the device may have different sizes and shapes. A surface size of the RF electrode contacting the patient (see lower part of the electrode 402a in FIG. 16) may be in a range between 1 $cm^2$ to 1200 $cm^2$ or between 10 $cm^2$ to 800 $cm^2$ or between 30 $cm^2$ to 300 $cm^2$ or 30 $cm^2$ to 100 $cm^2$.

Figure 11:
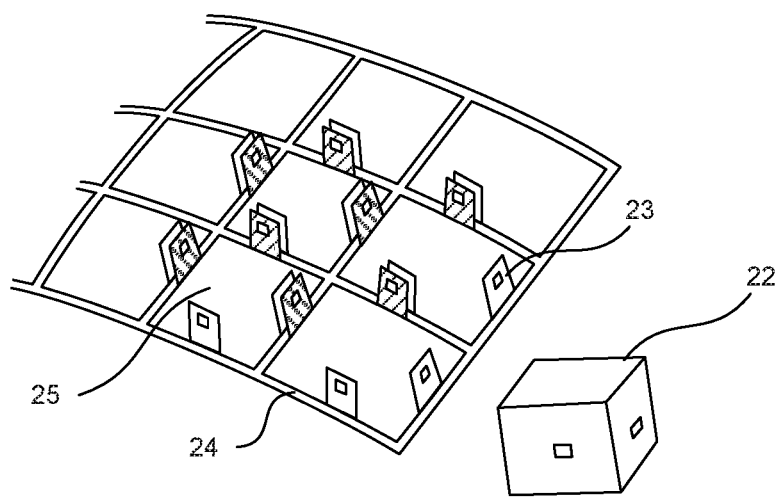
FIG. 11 illustrates one example of a supporting matrix and one applicator.

FIG. 11 illustrates one example of a supporting matrix and one applicator. The applicator 22 may have different sizes and shapes and may be attached by fastening member 23 to the supporting matrix 24 across one or more applicator spots 25. As a result, so-called plug and play methods may be used to modify the hardware pattern of the applicators attached to the patient and/or to the supporting matrix (sorting and/or choosing of the applicators). This plug and play method provides a large scale of modularity. The supporting matrix and/or any processor may recognize which applicator is positioned or fixed in which slot in the supporting matrix. Feedback sensor(s) and/or the user may also determine which body part is going to be treated.

In an exemplary embodiment the applicator, after connection to the supporting matrix, is identified by the master unit and the master unit is capable of recognizing applicator parameters including at least one of: the kind of treatment energy source(s) in the applicator, parameters adjustable for treatment, wear of the applicator, wear of components in the applicator, and the location of the applicator in the support matrix.

According to some embodiments the applicator's spot size and/or shape may be adjusted according the applicator design before and/or during the treatment. Some types of supporting matrix may enable an attached applicator to be arbitrarily positioned without limitation of the placed applicator's spots. Such a supporting matrix may fix applicator(s) to arbitrary applicator spots by a removable fastening member and/or chemical, magnetic, electrical, and/or suction mechanisms, by inserting an applicator into a pocket in the support matrix, by Velcro, by loop tape, by magnet, by tacks and/or by any other of one or more types of fastening member. Such a supporting matrix may also include multiple holes that enables mechanical fastening with a fastening member to an applicator fitted with a specific protrusion. According to some embodiments the supporting matrix may not be divided by any applicator spots.

Some parts of the supporting matrix may be made of flexible, elastic and/or rigid materials e.g.: polymeric materials, ceramics, textile materials, conductive parts and/or other materials. The supporting matrix may be at least partially flexible and/or elastic to provide improved contact with the patient body and/or set an appropriate working distance for one or more applicators.

The support matrix may also contain apertures of different sizes and shapes. The support matrix may include a system for moving the applicator to move across the belt area, one or more sensors, a processor and/or memory. In some embodiments a mechanism of moving attached applicators and/or treatment energy sources may be provided according to a defined pattern. A trail for the applicator may be created by some system of rails for moving one or more component of the supporting matrix (e.g: applicator may be moved along them by mechanical forces based on pressure and/or tensile forces) and/or by a rail created from conductive elements, and applicators may be moved along them by electric, magnetic and/or electromagnetic forces caused by powering such conductive elements.

Movement of one or more applicators and/or treatment energy sources across the patient body may also be provided by movement of the supporting matrix. Movement of the supporting matrix may be provided by expansion and/or shrinking of some parts of the supporting matrix and/or by moving the supporting matrix along a spacing object (e.g. by mechanical, electrical, magnetic and/or combination of these forces) and/or by attaching the supporting matrix to any other movable parts of the device (e.g.: mechanical arm, construction on rails etc.)

The supporting matrix may include conductive parts that may provide communication between e.g.: applicators, applicators and the control unit, applicator(s) and treatment units and/or applicator(s) and external devices. Conductive parts in the supporting matrix may also provide a power supply to the applicator(s). Applicator(s) may include one or more rechargeable batteries as a source of energy. These batteries may be recharged through the supporting matrix and/or through the spacing object.

According to another embodiment the supporting matrix may also determine the applicator(s) e.g.: location in the supporting matrix, type, contact with the supporting matrix, and distance from the patient's surface. The supporting matrix may also provide feedback information and/or other features.

This sheet may contain conductive components. A hardware pattern may be created by placement of the applicators into the belt (e.g. supporting matrix) attached to patient's body. According to one embodiment the master or control unit may propose ideal hardware and/or treatment patterns based on the selected treatment protocol in order to optimize selected treatment effect(s) of selected body part(s). The master or control unit may also take into account supportive information parameters of the patient like age, sex, weigh, height, BMI, skin type and others.

The master unit and/or control unit may also propose one or more treatment effects, treatment protocols and/or treatment patterns according to the hardware pattern of the belt. According to a specific embodiment the device may be able to select the treated body part and/or the device may be able to determine the body part according feedback information from at least one sensor.

A treatment pattern may be created in several possible ways. A treatment pattern may be created by movement of at least one treatment energy source(s) and/or applicator(s) across the patient's surface. Means of moving the treatment energy source(s) may be provided within the applicator and/or by moving one or more applicators. Means of moving the applicators may be provided e.g. within the supporting matrix that may include movable parts. Means of moving the applicator(s) and/or treatment energy sources across the patient's surface may be provided e.g.: by a movable component of the applicator and/or the supporting matrix pushed by air/liquid pressure, by electromotor, by electric and/or magnetic forces causing movement of a movable part of the applicator, movement of the supporting matrix, and/or movement of the entire applicator. Movement of the treatment energy source and/or the applicator may be based upon principles described in U.S. patent application Ser. No. 15/433,210 incorporated herein by reference.

According to a preferred embodiment the treatment pattern may be created by switching on/off or varying intensity of delivered treatment energy between individual and/or groups of treatment energy sources. Switching between treatment energy sources or varying intensity of delivered treatment energy between treatment energy sources may simulate movement of at least one treatment energy source guided by operator. The creation of said treatment pattern may be based on principles described in U.S. patent application Ser. No. 15/433,210 incorporated herein by reference.

Figure 17:
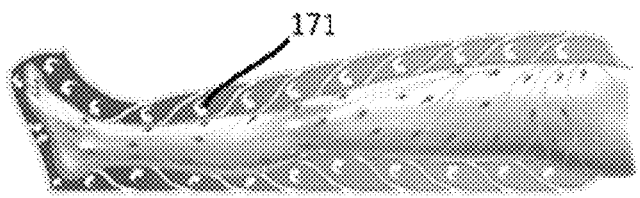
FIG. 17 illustrates influence of pressure on lymph and blood circulation.
Figure 18:
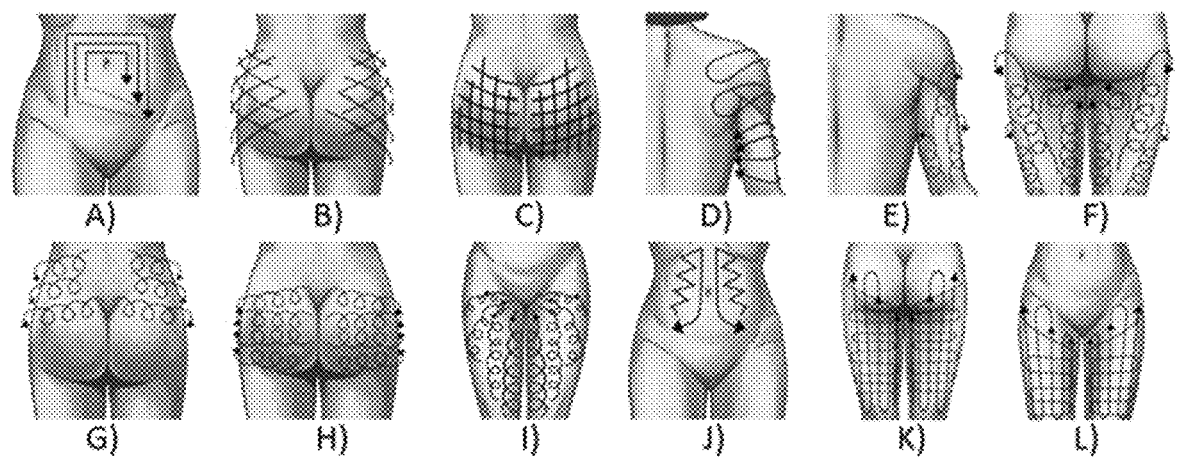
FIG. 18 illustrates treatment/massage patterns.

Massage and or other therapy may be provided in a pattern that is created by switching between previous and successive treatment energy sources. For example, in FIG. 17 a massage unit with pressure cells may create pressure individually, simultaneously, sequentially and/or with overlay in cooperation with one or more other elements changing pressure value. A treatment protocol may include information about a massage/treatment pattern e.g. which, when and/or for how long massage unit(s)/treatment unit(s) are switched on/off. Other characteristics of the treatment protocol for a defined massage/treatment pattern are parameters of delivered treatment energy source(s) and/or pressure parameters of the massage unit or group of massage units that are activated (switched on/off) according defined contiguity. A treatment pattern may simulate movements with an activated treatment energy source. FIG. 18 shows various treatment patterns. Treatment patterns may simulate: linear moves that may overlap e.g. as shown in FIG. 18 A)-C); curvilinear moves e.g. as shown in FIG. 18 D); curvilinear moves that may imitate progressive circular moves e.g. as shown in FIGS. 18 E)-I) and/or a combination of these as shown in FIGS. 18 J)-L).

Massage/treatment patterns in some treatment protocols may simulate massage/treatment provided by a physiotherapist and may enhance massage/treatment provided by a physiotherapist. The present apparatus and methods are not limited to just the two hands of a physiotherapist, or by the strength and fatigue of a physiotherapist. Massage provided by the present designs may also be provided in a different manner than applied mechanical pressure e.g. acoustic waves that may be more targeted and/or may selectively provide massage of deep soft tissue layers without influencing upper soft tissue layers that a physiotherapist is not able to provide. This massage/treatment pattern may change during the treatment.

Various treatment patterns and pressure gradients may be achieved by a treatment sleeve comprising a plurality of treatment energy sources and/or elements changing pressure value arranged in e.g. a line or matrix by providing successive therapy. Successive and previous treatment energy sources may be any kind of treatment energy sources. The successive and the previous treatment energy sources and/or equivalently successive and previous elements changing pressure value must comply with the prescribed requirements:

The successive and the previous treatment energy sources provide variable output power during treatment; the successive treatment energy source provides the same treatment therapy as the previous treatment energy source; the successive treatment energy source is included in the same treatment sleeve as the previous treatment energy source; and the successive treatment energy source is the source which starts to increase the output power value after the previous treatment energy source increases its output power value.

According to one embodiment more than one successive treatment energy source may increase output power at the same time.

It is possible to designate more than one treatment energy source as the previous treatment energy source that is distinguished from the previous treatment energy source for one specific successive treatment energy source and it is the one with the shortest distance from the successive treatment energy source.

Designation of a previous and successive treatment energy source is changing during switching on/off or changing output power between individual treatment energy sources in order to simulate movement of the treatment energy during the therapy.

When a successive treatment energy source is activated, a previous treatment energy source may or may not be still activated.

A treatment energy source is considered as activated when it is providing any wanted treatment energy type (any treatment therapy) to the patient's soft tissue.

Successive therapy creates a pattern and may be defined relative to successive therapy speed. The successive therapy speed describes a speed of moving, changed intensity of treatment energy source/elements, and changing pressure value along the treatment pattern. Successive treatment therapy may be provided by switching between previous and successive treatment energy sources and/or changing output power between previous and successive treatment energy sources. The successive therapy speed is then counted as a division of distance between central parts of previous and successive treatment energy sources and time delay between starts of output energy rising of previous and successive treatment energy sources. The successive therapy may also be provided by moving the treatment energy source relative to the patient's surface. Then the successive therapy speed is moving speed of the treatment energy source. According to still another embodiment the successive therapy may be achieved by changing spatial coordinates of a focal spot across the treated body area (changing of focus depth in the soft tissue is not included). Then successive therapy speed is speed of moving a center of the focal spot across the patient soft tissue. The successive therapy speed is measured in units of $cm \cdot s^{-1}$.

Average successive therapy speed may be in range between 0.1 $cm \cdot s^{-1}$ and 50 $cm \cdot s^{-1}$ or more preferably in range between 1 $cm \cdot s^{-1}$ to 30 $cm \cdot s^{-1}$ or the most preferably in range between 5 $cm \cdot s^{-1}$ to 15 $cm \cdot s^{-1}$.

The treatment pattern created by at least one, but more preferably, at least two types of treatment energies by at least two treatment energy sources is characterized by at least one, more preferably, at least two target spots of specific and/or different treatment energy sources that may vary treatment energy intensities with respect to time and/or spatial coordinates—usually located within the patient's tissue. The target spot is a location where treatment energy is delivered, and which has an absolute value of provided treatment energy intensity above zero. The target spot may be created by providing focused and/or non-focused treatment energy. The center of a target spot is a spatial coordinate where the absolute value of the provided treatment energy intensity is the highest (e.g. center of the treatment energy source). In one embodiment the treatment pattern may be created by a continuous or discontinuous trajectory of the target spot(s) across spatial coordinates. The target spot(s) may vary intensity of delivered treatment energy during the trajectory described by the treatment pattern. Movement of the target spot may be provided by movement of at least one treatment energy source that usually creates the continuous trajectory of target spot(s) and/or by varying treatment energy intensities between at least two treatment energy sources wherein the target spots may overlap and create continuous trajectory and/or may not overlap that creates a discontinuous trajectory of the target spot described by treatment pattern. Changing spatial coordinates of the center(s) of target spot(s) across patient's tissue during the time may be described by the treatment pattern speed. The treatment pattern speed may be also described as a ratio of the target spot's distance and time delay. A spot's distance is the distance between the centers of the target spots of at least two of the nearest treatment energy sources reaching maximum treatment energy intensity during shortest time delay. The time delay may be described as a time delay between above mentioned centers of target spots reaching their absolute maximum values of treatment energy intensities. The average treatment pattern speed may be in the range between 0.1 cm·s$^{-1}$ and 50 cm·s$^{-1}$ or more preferably in a range between 1 cm·s$^{-1}$ to 30 cm·s$^{-1}$ or most preferably in a range between 2 cm·s$^{-1}$ to 15 cm·s$^{-1}$.

The treatment pattern speed may be constant and/or may vary during one treatment pattern.

The treatment pattern provided by a first type of treatment energy may be also accompanied by other types of one or more treatment energies provided to the patient's tissue. Such other treatment energies may follow the treatment pattern of the first treatment energy with the same or a different treatment pattern speed and/or may follow different treatment pattern(s).

Treatment patterns may also be created by varying treatment energy intensities of multiple treatment energy sources that reach their maximums of absolute value of treatment energy intensities at the same time. According to such an example, the treatment pattern speed may be described, as was described above, as a ratio of a target spot's distance and time delay.

The treatment pattern may change during one treatment based on one or more treatment protocols.

During one treatment, a patient may be provided one or more treatment patterns simultaneously and the treatment pattern may also overlap and/or build on itself.

Figure 8:
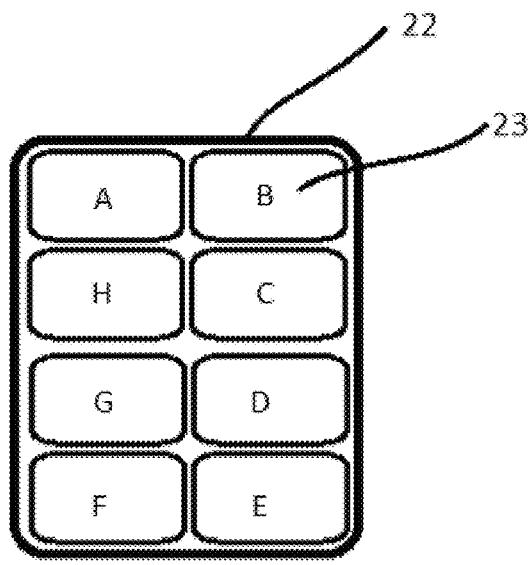
FIG. 8 illustrates the active surface of an applicator with multiple treatment energy sources.

An applicator including more than one treatment energy source may create its own small treatment pattern by switching between individual treatment energy sources. The small treatment pattern created by one applicator may be part of bigger treatment pattern created by switching between individual applicators. In FIG. 8 where 22 symbolizes the applicator's active surface with multiple treatment energy sources A-H and 23 symbolizes one of the treatment energy sources. The applicator may contain treatment energy sources with different shapes. The number of treatment energy sources in one applicator is not limited. Switching on/off between treatment energy sources, changing of the treatment energy intensity between treatment energy sources and/or movement of the treatment energy sources during the treatment may be defined by treatment protocol. The treatment energy sources of at least one applicator can work simultaneously, with some overlay and/or sequentially during the treatment. Also one or more treatment parameters of the procedure may be adjusted before and/or during the treatment.

The applicator and/or the treatment energy source may provide multiple treatment effects. According to one embodiment one applicator may include treatment energy sources producing one or more types of treatment energies e.g. one treatment energy source may produce shock waves, ultrasound and/or acoustic waves during one treatment.

Time intervals between the power amplitudes of delivering treatment energy to the patient's body by individual treatment energy sources may overlay and/or may be divided by a pause time interval in the range between 01 ms to 15 s or 1 ms to 5 s or 100 ms to 3 s.

Figure 15:
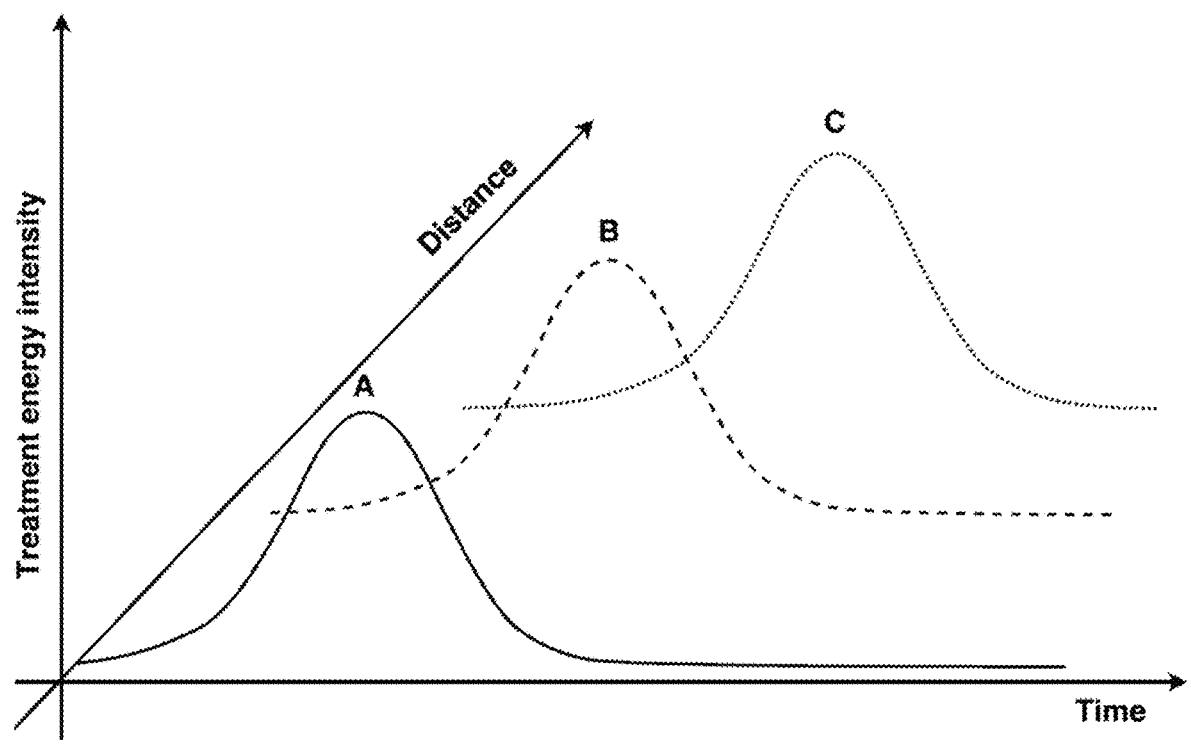
FIG. 15 illustrates a possible example of three time-domain functions of treatment energy intensities provided by individual treatment energy sources arranged in a hardware pattern.

FIG. 8 describes one possible positioning of treatment energy sources. The respective treatment energy sources may provide a treatment pattern by varying intensity of delivered treatment energy between the respective treatment energy sources as depicted in FIG. 15. Treatment energy source A may temporarily increase intensity of provided treatment energy A to patient's body (see peak A). After treatment energy intensity A rises above the initial treatment energy intensity value, treatment energy intensity B provided by treatment energy source B (see peak B) may also start to temporarily rise. The same principle as was described for treatment energy source A and B may be repeated for treatment energy sources C (see peak) and D, E, F, G, and H and that may create a circular treatment pattern with a clockwise direction that may be repeatedly used. The treatment pattern speed between treatment energy sources A and B according to FIG. 15 may be quantified as the distance between maximums of peaks A and B in a ratio with the time delay between when peak A and peak B reach their maximums.

The various other treatment patterns as described in this document may be used.

According to another embodiment peaks A, B and/or C in the FIG. 15 may represent different types of treatment energies e.g.: RF, ultrasound and/or shock wave. Peaks A, B and/or C may have the same and/or different profiles, maximal values and/or integral values. A treatment energy intensity peak may have no overlap and/or may at least partially overlap in terms of spatial coordinates and/or time.

According to the treatment pattern in FIG. 15, the peak of the first treatment energy intensity (peak A) may start to decline sooner, at the same time or after the second treatment energy intensity (peak B) starts to decline and/or reaches its maximum intensity value.

Also target spots created by the same and/or different treatment energy types during a treatment pattern may have no overlap and/or may at least partially overlap in the patient's tissue.

According to one preferred embodiment a pattern with at least two different energy sources providing different treatment energy may be used.

Figure 9:
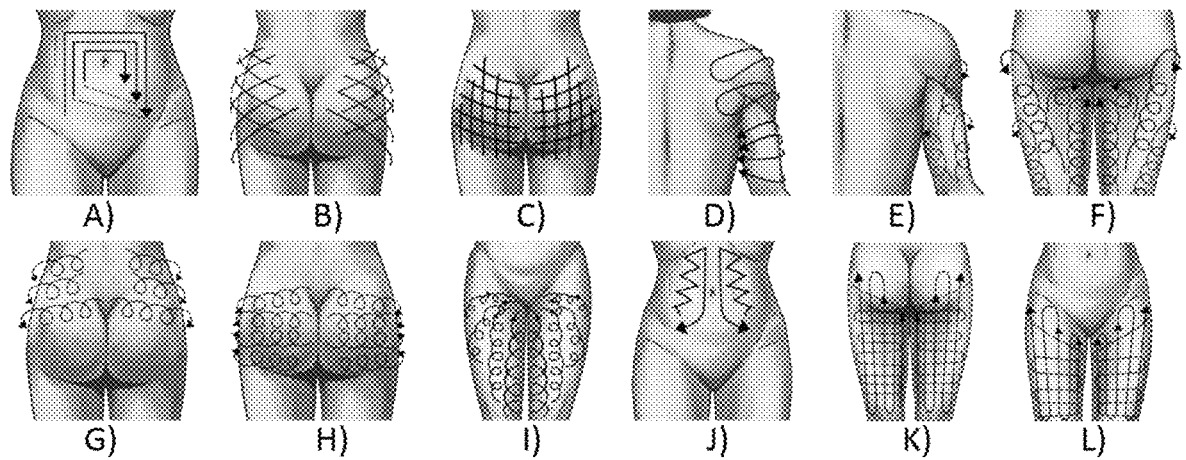
FIG. 9 demonstrates several treatment patterns provided across the patient's surface.

The pattern with at least two different energy sources providing different treatment energies may provide a synergistic effect by influencing the treatment results. One illustrative example of such synergy may be a pattern consisting of RF and focused ultrasound energy sources where the ultrasound energy source provides heating in the target spot and then the RF is more readily absorbed by the preheated tissues, while continually simulating movement according to the chosen pattern Possible treatment patterns (see FIG. 9) may simulate linear movements of treatment energy source(s) across the patient's surface (See FIG. 9 A-C). FIG. 9 D simulates curvilinear movements, FIGS. 9 E-I simulates several types of circular movements, and/or FIGS. 9 J-L simulates a combination of linear and curvilinear movements.

The treatment pattern may not be limited only by movement of the treatment energy target spot in two dimensional movements with respect to patient's surface. The treatment pattern may determine the depth of the treatment energy target spot. One illustrative example may be a pattern consisting of RF and focused ultrasound energy sources where the focused ultrasound energy source provides heating in the target spot at one depth and then the RF is more readily absorbed by the preheated tissues, while continually simulating the movement according to the chosen pattern, which simulates movement of the target spot in tissue in one, more preferably two, or most preferably three dimensions. The depth and planar location of the target spot may vary in time based on selected treatment protocol.

Figure 10:
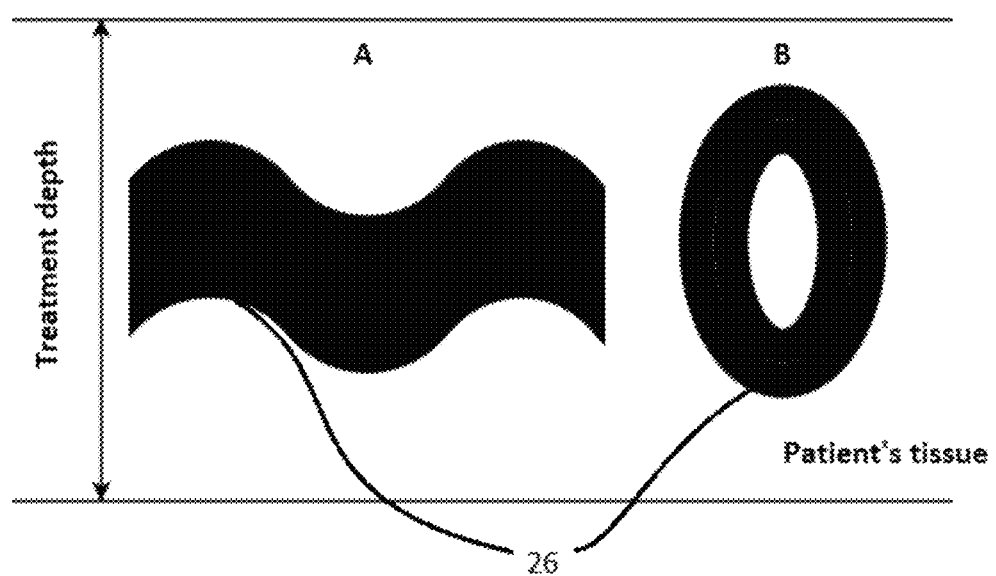
FIGS. 10A and B illustrate treatment patterns provided into a depth of the patient's tissue.

A treatment pattern with and/or without a defined treatment depth pattern may be cyclically repeated. FIG. 10 A illustrates one possible example of a short sequence of treatment patterns with varied treatment energy focus depths 26 by changing the horizontal coordination of a treatment energy target spot in the patient's tissue. Horizontal coordinates are parallel to patient's surface curvature under the belt at every space coordinate under the belt. For example horizontal coordinates in the patient's hip area according to some patients' body types may be described as a convex surface area in Cartesian coordinates. FIG. 10 B illustrates one possible example of a treatment pattern with varied treatment energy focus depth 26 by changing the horizontal coordination in the patient's tissue over time. Treatment energy focus depth 26 may be also varied during the time of the treatment without regard to changing horizontal coordinates of the treatment energy target spot. The depth of the treatment energy target spot may be varied also for non-focused treatment energy e.g. by changing the intensity of delivered treatment energy, changing the wavelength, polarization of treatment energy, changing the distance between electrodes providing RF treatment energy and/or by changing other parameters of delivered treatment energy to the patient's body.

The depth of a treatment energy target spot may be varied also by changing parameters of patient's tissue for example by providing another treatment energy e.g. heating or cooling of the patient's tissue that may increase penetration of the RF waves, or by applying an electric field that may influence dielectric behavior of the patient's tissue.

Various kinds of treatment patterns may be provided by various kinds of hardware patterns. Cooperation of a hardware pattern and a treatment pattern may significantly improve treatment result(s), shorten treatment time and/or may increase treatment safety. Exemplary variants of hardware patterns providing a treatment pattern are provided below. According one exemplary variant, one option may be sequential and/or simultaneous application of one or more treatment energies heating the patient's tissue and/or damage tissue cells with treatment energy that accelerates metabolism, blood flow, lymph flow and/or accelerates the removal of damaged cells. A simulated movement trajectory may be like what is illustrated in FIGS. 9 A-L. An example of such a treatment pattern may be alternately placing treatment energy sources providing e.g.: RF, shock waves, ultrasound, light; and treatment energy sources providing massage and/or muscle stimulation like e.g. a suction mechanism, a muscle stimulating magnetic field, a muscle stimulating electrode, a movable massage element providing mechanical pressure and/or any other.

According to one exemplary variant, one option may be using one or more treatment energy that heats patient's tissue and/or damaged tissue cells in combination with at least one treatment energy that accelerates metabolism, blood flow, lymph flow and/or accelerates the removal of damaged cells. The combination of such at least two different treatment energies may be simultaneous, with some overlay, sequential and/or may be applied in close proximity to allow the synergistic effect of at least two different types of treatment energies. An applicator and/or treatment energy sources in an applicator may be distributed in a 2D and/or 3D matrix. For example applicators including different types of treatment energy sources may be placed in close proximity to the supporting matrix and/or to the patient's body and coordinated variation of treatment energy intensities may simulate movement of at least one applicator as it is illustrated in the FIGS. 9 A-L.

An example of such a treatment pattern may be alternately placing treatment energy sources providing e.g.: RF, ultrasound, shock wave or light in combination with treatment energy sources providing e.g.: acoustic wave, massage and/or muscle stimulation by a suction mechanism, a magnetic field, a current, a movable massage element providing mechanical pressure and/or any other.

Figure 13:
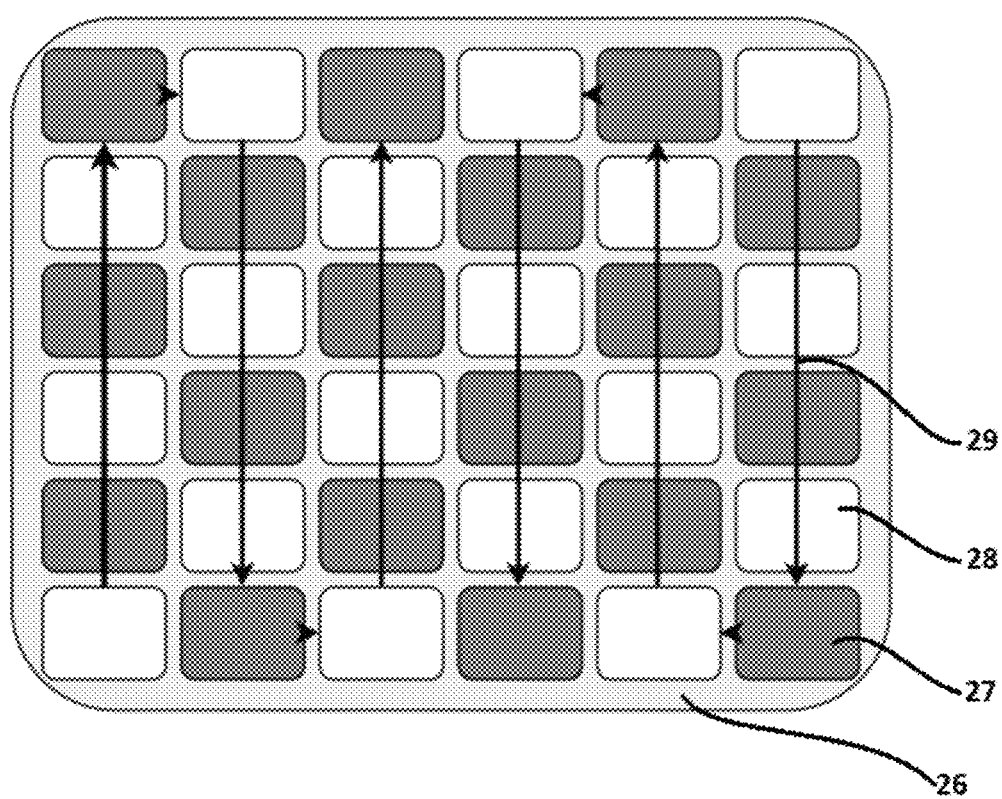
FIG. 13 illustrates one possible symmetric hardware and treatment pattern.
Figure 14:
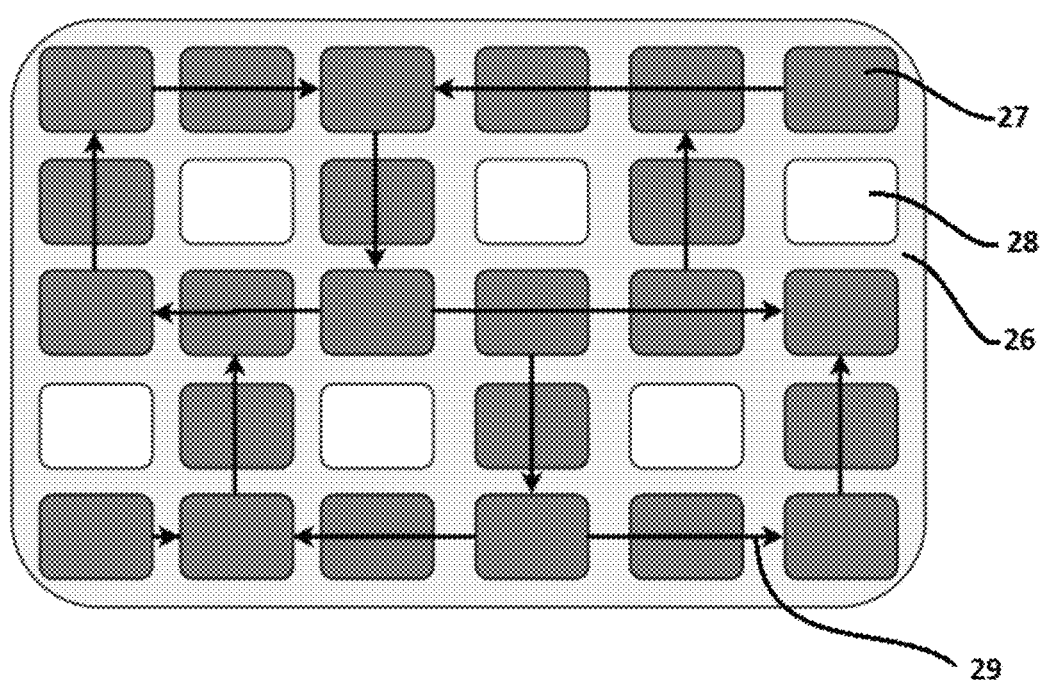
FIG. 14 illustrates one possible symmetric hardware pattern and asymmetric treatment pattern.

The placement of different treatment energy sources/applicators may be one of the most important parameters of the treatment. FIGS. 13 and 14 illustrate two types of treatment patterns. FIG. 13 illustrates alternately placed treatment energy sources 27 providing heating of the patient's tissue, creating cell damage and/or tissue structural damage e.g. by: RF, ultrasound, shock wave or light etc. in combination with treatment energy sources 28 providing acoustic wave, massage, stimulation of lymph flow, blood flow and/or metabolism stimulation. Treatment energy sources 27 and 28 may be attached to a supporting matrix 26. Arrows 29 symbolize the direction of the treatment pattern and orientation of the speed of the treatment pattern therapy.

FIG. 13 provides a symmetric treatment pattern simulating linear movement of two treatment energy sources. According to another example treatment energy sources 27 may be placed around the treatment energy sources 28 (see FIG. 14). Symmetric placement of treatment energy sources and/or applicators may create also asymmetric and/or partially symmetric treatment patterns depending on the resulting pattern created by varying intensities between multiple treatment energy sources at the same time (see arrows 29). The resulting pattern according to arrows 29 in the FIG. 14 imitate partial symmetric circular movement by multiple treatment energy sources.

According to FIG. 14 treatment energy intensities provided by treatment energy sources 27 may simulate circular movements and treatment energy sources 28 may provide continual and/or pulsed blood, lymph and/or metabolism stimulation.

According to another embodiment the treatment pattern(s) may also be created by treatment energy sources that change the location of treatment energy target spots in the patient's tissue by its movement. The changes may also be target spot volume, target spot depth, target spot shape and/or target spot coordinates according to the horizontal plane in the patient's tissue.

The treatment patterns described in FIGS. 13 and 14 are not limiting examples.

According to one exemplary variant one or more treatment energies may provide treatment of hypodermal tissue and one or more different treatment energies may provide treatment of epidermal or dermal tissue. The combination of such at least two different treatment energies may be simultaneous, with some overlay, or sequential, ensuring faster treatment of more than one tissue problem. An example of such a treatment pattern may include use of a treatment energy source providing hypodermal treatment by RF, ultrasound, shock wave, light or magnet and a treatment energy source providing epidermal or dermal treatment by light, plasma, or RF.

According to another exemplary variant one or more treatment energies may provide treatment of epidermal tissue and one or more different treatment energies may provide treatment of dermal tissue. The combination of such at least two different treatment energies may be simultaneous, with some overlay, or sequential, ensuring faster treatment of more than one tissue problem. One example of such treatment a pattern may include use of treatment energy source providing epidermal treatment by light or plasma: and a treatment energy source providing epidermal or dermal treatment by RF, ultrasound, shock wave, or light.

The described variants may also damage cells and/or tissue structure by a first treatment energy source and accelerate healing of the tissue by the second treatment energy source.

Attachment of the applicator to the belt or the belt to the patient may be provided by: gravitational force, by roughness of contact surfaces, by electrical forces, by magnetic forces, by chemical bonds (e.g. interaction between polar molecular groups on at least one of the contact surfaces), via fastening member(s) e.g. working on a clam mechanism and/or any combination thereof. A fastening member may be a permanent or removable part of any applicator, supporting matrix, spacing object and/or any other part of the device (e.g. treatment unit(s) and/or mother case). A fastening member may be an adhesive polymer or copolymer (e.g. poly(styrene/ethylene/butylene) which is located at one or more contact sides of the fastening member. A fastening member may also be designed as: rails, a sticky layer between two contact sides, elastic, partially elastic and/or non-elastic strips, lace, Velcro, a zipper, a snap, a clamp, tacks, a member creating lower air pressure between contact surfaces e.g.: by a suction mechanism, by a layer providing interaction between polar and/or non-polar groups on the contact surfaces and or a member using physical means (e.g.: electric, magnetic forces), chemical means, or a mechanical interaction between fastening member(s), parts of the device and/or between patient surface.

Fastening members may have different sizes, shapes and in one embodiment may be a combination of different types of fastening members.

The applicator(s) may be attached at the optimal working distance by a fastening member designed as one or more strips located on the front and/or back side of the applicator. Suitable elastic materials are elastomers or also elastic fabrics. The elastic belt material also adapts to respiratory movements and/or other movements of the patient. The fastening member designed as strips may also include conductive component(s) that may be connected and/or communicate with the supporting matrix and/or other part(s) of the device. Such conductive components may also recharge one or more applicator(s) and/or the supporting matrix.

The supporting matrix may hold one or more applicators in close contact with patient's body surface and/or it may also hold one or more applicators at an optimal working distance from the patient surface. The patient's surface is typically the epidermis of the patient. However, the patient's surface may alternatively be some spacing object e.g.: clothing worn over the skin, a sheet, a pad or other thin (0.1-2 mm) covering over the skin, and/or a thicker spacing object. The spacing object may provide a suitable working distance for the applicators, may provide heating/cooling of the patient body, may provide massage of patient's soft tissue, may provide several modifications of delivered signal to the patient soft tissue (e.g.: polarization), filtration of a provided signal to the soft tissue, better transfer of a signal to the soft tissue, changed direction of the pointing vector of a provided electromagnetic field, prevention of an edge effect and/or any others as described in U.S. Provisional Application No. 62/331,072, incorporated herein by reference. A spacing object may be located between any parts of the device e.g. between the supporting matrix and applicator(s) and/or between the patient and parts of the device (e.g. between the patient and supporting matrix and/or between the patient and applicator(s)). Because of mechanical, structural, physical and/or chemical properties of this spacing object, the spacing object may provide and/or improve attachment of any parts of the device and/or parts of the device and the patient body surface together.

A filler of the spacing object may be gaseous, liquid and/or from solid material. A spacing object may be composed of any kind of ceramic, plastic material, rubber, textile material, metal, polymeric materials and/or any other material that improves any therapy parameter(s). In some embodiments it may be important to choose a material and/or construction of the object to provide a stable form and/or shape of the spacing object. A spacing object may be flexible and/or rigid and may imitate curves of the body contour.

Treatment by electromagnetic field and spacing object enabling changing of temperature and/or other parameters (permittivity, permeability, conductivity and/or their parameters) and/or its one or more component may create temperature gradients across the soft tissue of the patient. This is very important because tissue dielectric parameters (e.g. impedance, conductivity and/or other related dielectric parameters) change with different temperature and frequency of applied electromagnetic waves. Targeting of thermal gradient by applied electromagnetic field and continuous but more preferably sequential heating and/or cooling of the patient surface by the spacing object may improve the effect of the treatment and minimize health risk.

Filler of the spacing object may provide polarization and/or reflection and/or may focus delivered electromagnetic energy and/or may be used as a filter of electromagnetic waves and/or may adjust an orientation of the wave vector of the electromagnetic wave as was mentioned below. Polarization of the electromagnetic wave has a different impact on different molecules and environments, so polarization may influence absorption, dispersion, penetration, targeting and/or reflection of the electromagnetic wave. Polarization of the electromagnetic wave may be created by anisotropic arrangement of dielectric films (e.g. by poly (vinyl alcohol) doped by iodine or other substances based on dichroic polarizers principle) and/or by principle of the phase retardation plate and/or by material and/or geometry of the antenna. Some polarization and reflection elements may have crucial influence to prevent creating hot spots due to changing of the orientation of the wave vector and selective modification of the component of the electromagnetic wave.

Cooling or heating of tissue may be ensured by a spacing object filled with a suitable substance (mostly liquid or gaseous substances e.g. water, water doped NaCl, ethanol, air, $N_2$, $CO_2$, air and others). The parameters of the substance such as temperature, viscosity, flow etc. may be monitored by one or more sensors (e.g. temperature and/or viscosity sensors and/or sensor measure inducted currents or chemical changes of the substance).

Figure 19:
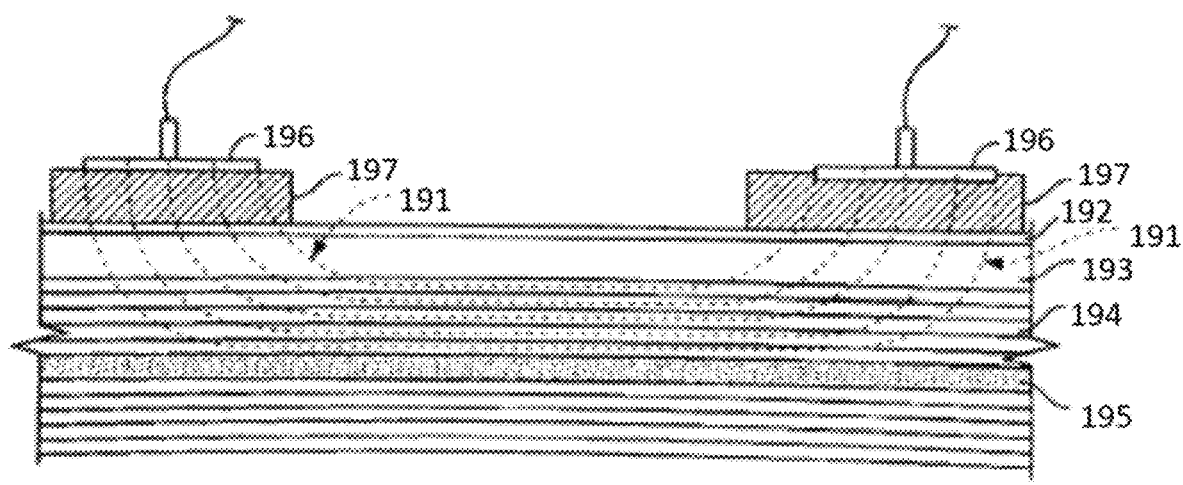
FIG. 19 is a schematic diagram of a system for controlled deep heating of sub dermal tissues.

FIG. 19 is a schematic representation of a heat distribution under the skin. One or more applicators 196 create an electromagnetic field. This electromagnetic field crosses through the skin 192, subcutaneous fat 193 and muscle 194 or the bone 195. Capacitive applicators 196 provide deep heating, which heats selectively only structures with low volume of water. A spacer 197 such as an object, towel, gauze pad, foam pad, cloth pad or other porous or air permeable materials may be placed on the skin, with the applicator then placed on top of the spacer 197. The spacer may be made from a three-dimensional material with high air permeability formed by two square fabrics with preferably low square densities connected by tough filaments. This automatically sets the separation distance between the applicator and the skin, and prevents the applicator from touching the skin. The spacer 197 may be made of various dielectric or electrically non-conductive materials. The spacer 197 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

The belt may at least partly encircle any part of the patient's torso and/or limb.

Feedback information may be collected by different types of sensors and may have different characteristics (e.g.: biological, chemical, physical etc). One or more sensors may be located in the supporting matrix, in one or more applicator(s) and/or may be located externally outside of the belt (e.g.: optical, sonic and/or others located around a patient). One or more sensors may control treatment parameters (e.g.: the intensity of delivered energy into the tissue, the sequence of applied treatment energy, changed parameters of the delivered signal, switching on/off of different treatment energy sources and/or others). The device may contain different types of sensors for monitoring device parameters, monitoring of the body via biological, physical, chemical and/or other parameters (e.g. an electrochemical sensor, a biosensor, a biochemical sensor, a temperature sensor, a sensor for measuring the distance of an applicator from the patient surface, from some area of the patient soft tissue and/or from other applicator, a sensor to determine the position of the device with regard to patient's body part, a sensor for recognition of the applicator orientation in 3D space, a rotational orientation sensor, a sorption sensor, a pH sensor, a voltage sensor, a detector of moving velocity and/or a change of treatment energy source position, a sensor to detect a change of focus target area of the treatment energy, a photo sensor, a sensor measuring fluid viscosity, a camera, a sensor for measuring fluorescence of the patient surface, a sound detector, a current sensor, a sensor for measuring of specific heat capacity of human/animal tissue, a sensor for measuring the value of a magnetic field, a sensor for measuring impedance, permittivity, conductivity, or susceptibility). The device may also contain any suitable sensor or sensors for measuring biological parameters and/or any combination thereof (e.g.: a sensor for measuring dermal tensile forces; a sensor for measuring the activity of the muscle; a sensor for measuring muscle contraction forces; a sensor for measuring pulse of the patient; a sensor for measuring skin elasticity). The device may also include at least one contact sensor for monitoring applicator contact with the body surface of the patient. The supporting matrix may also recognize the type and/or location of one or more of the different applicators attached to the supporting matrix.

The applicator(s) may be able to communicate with each other and/or other parts of the device (e.g. an external device, a control unit, a treatment unit and/or others) as was mentioned above. This communication may provide information from feedback sensors, about position of one or more applicators, 3D orientation of the applicator(s), information about contact of the applicator(s) with the patient and/or the supporting matrix, distance from the patient surface, parameters of the treatment protocol, parameters of each applicator and/or other information from one or more sensors. Data from the different applicators and/or types of sensors may provide complex information about the treatment and/or the treated soft tissue. Information from the sensors may be used to determine which part of the patient is treated, determine the exact composition of treated tissue and/or changes in the patient's tissue during the time of the treatment. These sensors may cooperate with one or more treatment energy sources provided and may be used as an imaging device of the surface and/or deeper layers of the patient soft tissue. The imaging system of the soft tissue before and/or during the treatment may improve safety of the treatment, determine when the treatment is complete, monitor treatment process and/or progress of the treatment. This processed data may be used for adjusting parameters of the treatment procedure, may activate other treatment energy source(s) and/or one or more treatment protocols (e.g. activate massage, cooling, heating and/or others) and/or change any other parameter of the treatment protocol. This data may also warn the operator and may be used as a prevention of health risk and/or may prevent damage to any part of the device.

The treatment protocol may include several instructions that define treatment of one or more treatment energy sources and/or applicator(s). The treatment protocol may include information about e.g.: the treatment pattern, the treatment pattern speed, which treatment energy source(s) are switched on/off and/or parameters of individual treatment energies produced by individual treatment energy source(s). The treatment protocol may also include information about applicator(s) and/or the treatment energy source hardware pattern. The treatment protocol may also include information about the system of collecting feedback information e.g. which sensors communicate with which part of the device. According to some embodiments the treatment protocol may also include information on how parts of the device communicate with each other, how information will be processed during the treatment, or which parts of the device and/or treatment protocol may also define priority of commands during device communications. Other examples of information that may be included in treatment protocol include: applied treatment effect(s), shapes and types of a delivered signal of treatment energy into the tissue (symmetrical; asymmetrical; polarized; non-polarized; continual or sequences of signal pulses; timing of the delivered signal; shape of the signal: sine, square, triangle, saw tooth and/or others), the defined pulse sequence intensity of delivered energy, polarization of a delivered electro-magnetic signal, the remaining time of treatment procedure, threshold parameters, the time and/or sequence of heating/cooling of the soft tissue and/or other parameters that influence treating of the soft tissue by one applicator (e.g.: geometry and position if it is possible to change this parameter and/or other parameters).

Figure 12:
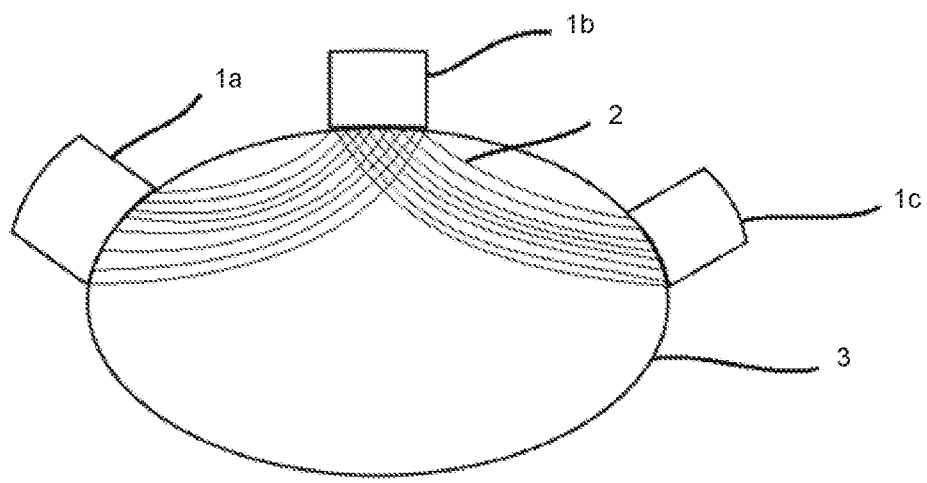
FIG. 12 illustrates a multipolar treatment of three cooperating applicators.

Several applicators may cooperate with each other. FIG. 12 describes cooperation of multiple applicators 1*a*, 1*b*, 1*c* that may provide treatment energy or energies (e.g. multipolar RF therapy symbolized by field lines 2) to the patient 3. Cooperation of treatment energy sources providing different treatment energies (e.g.: RF, ultrasound, light, acoustic wave, shock wave, plasma, mechanical massage, cooling/heating, electric field, electric current, magnetic field and/or other treatment energy sources) may be used for better targeting of the delivered therapy, better focusing of a delivered signal, the creation of some gradient in the soft tissue (e.g. thermal gradient, etc.), or better homogeneity of provided therapy across a large patient area and/or volume of the soft tissue.

According to one embodiment, the cooperation of multiple applicators and/or treatment energy sources may increase treatment variability (e.g. treatment depth, focusing, preventing hot spots) and may provide lower intensity of treatment energy without lowering treatment result, since the electrode of each applicator and/or treatment energy source represents one pole of a multipolar treatment.

Cooperation between applicators and/or treatment energy sources may include transferring of treatment energy or communication information and/or one applicator may provide a power supply to one or more other applicators.

The presented description of the device is not intended to limit the invention to these embodiments, but rather to enable any person skilled in the art to make and use this invention.

The invention claimed is:

1. A method of improving a visual appearance of a patient with a modular treatment device, comprising:
   connecting a first treatment unit and a second treatment unit to a mother case;
   wherein the mother case includes a control unit and slots;
   wherein the first and second treatment units are removably connected to the mother case in the slots;
   using the control unit to detect and configure the first and second treatment units in the mother case,
   wherein the control unit includes a processor and a memory;
   wherein the control unit contains one or more predefined treatment protocols; and
   wherein the control unit is configured to control the first and second treatment units;
   connecting a first applicator to the first treatment unit, connecting a second applicator to the second treatment unit and coupling the first and second applicators to a body part of the patient;
   wherein the first applicator includes a first treatment energy source; and
   wherein the second applicator includes a second treatment energy source;
   providing the one or more predefined treatment protocols to a user based on a detection of the first and/or the second treatment unit;
   generating treatment energies with the first and second treatment units,
   wherein each of the first and second treatment units generates a different type of the treatment energy;
   providing a first treatment energy to the body part of the patient with the first treatment energy source;
   providing a second treatment energy to the body part of the patient with the second treatment energy source; and
   guiding the treatment with the control unit in order to improve the visual appearance of the patient.

2. The method of claim 1, wherein the first or second treatment energy is one of: a radio-frequency, a plasma, an ultrasound, acoustic waves, shock waves, a light, an electric current, a magnetic field, a positive or negative pressure, a heating or a cooling.

3. The method of claim 1, further including applying the first treatment energy and the second treatment energy to the body part of the patient simultaneously during the treatment.

4. The method of claim 3, wherein the first treatment energy and the second treatment energy are applied to the body part of the patient at the same time, sequentially or with overlay according to the selected treatment protocol.

5. The method of claim 1, further including coupling the first and second applicators to the body part of the patient with a belt;
   wherein the device is configured to be self-operated without needing intervention by professional medical staff after the treatment begins.

6. The method of claim 5, wherein the belt is flexible or partly elastic.

7. The method of claim 1, further including attaching the first or the second applicator to the body part of the patient with a fastening member;
   wherein the fastening member is a part of the first or the second applicator; and
   wherein the fastening member is an adhesive polymer or copolymer.

8. The method of claim 1, wherein the body part of the patient includes one of: a bra fat area, buttocks, saddlebags, love handles, an abdomen, hips, thighs, arms, a limb, a back, a cervical body part and also a muscle or muscle group of the mentioned body parts, which is treated in order to improve the visual appearance of the patient.

9. The method of claim 1, further including a third treatment unit generating a third treatment energy different from the first and second treatment energies;
   wherein the third treatment unit is removably connected to the slot of the mother case by the user;
   detecting the third treatment unit in the mother case with the control unit;
   connecting a third applicator to the third treatment unit, wherein the third applicator includes a third treatment energy source;
   providing an additional treatment protocol to the user based on the detection of the third treatment unit by the control unit; and
   providing the third treatment energy to the body of the patient with the third treatment energy source.

10. The method of claim 1, further including selecting the treatment protocol based on at least one of: a required treatment effect or age, sex, weight, height, BMI or skin type of the patient.

11. The method of claim 1, further including transmitting information about the selected treatment protocol to a billing system based on credits subtraction from the user; and
   subtracting credits in the billing system according to the selected treatment protocol.

12. The method of claim 1, further including transferring a communication data by a communication medium between the device and the user or the patient,
   wherein the communication medium is a wire, any conductive connection, server, storage cloud, network, RF waves, acoustic waves, optic waves, GSM, 3G, 4G, HUB switch, Bluetooth or Wi-Fi.

13. The method of claim 12, wherein an information provided in the communication data between the device and the user is one of: a type of the treatment protocol, the treatment effect, treatment parameters, a feedback information, a schedule of treatments or recommendations of behavior before and after the treatment.

14. The method of claim 12, further including downloading an app for the patient to an external device,
wherein the app communicates with the device via the communication medium, and
wherein the app displays treatment protocol information selected from: progress of the treatment, the treated body part, a remaining time of the treatment, a heart rate, a temperature of the patient's body, provided type of the treatment energy, the desired treatment effect or a comparison of patient's body parameters against previous treatment.

15. The method of claim 12, further including providing a communication data between the device and a service,
wherein the service has authorized access to information about the device; and
wherein the communication data between the device and the service includes the wear and/or consumption of the device and its components, possible optimization/actualization of a software of the device and its parts, errors in the device, or providing apps for connections to other external devices.

16. The method of claim 12, further including protecting the communication data with a security.

17. A method of improving a visual appearance of a patient with a modular treatment device, comprising:
connecting a first treatment unit and a second treatment unit to a mother case;
wherein the mother case includes a control unit and slots;
wherein the first and second treatment units are removably connected to the slots of the mother case by a user, and
wherein the first and second treatment units are interconnected;
detecting and configuring the first treatment unit and the second treatment unit with the control unit,
wherein the control unit includes a processor and a memory;
wherein the control unit contains one or more predefined treatment protocols; and
wherein the control unit controls the first and second treatment units;
connecting a first applicator to the first and second treatment units and coupling the first applicator to a body part of the patient, wherein
the first applicator includes a first treatment energy source and a second treatment energy source;
providing the one or more predefined treatment protocols to the user based on a detection of the first and second treatment units;
generating a first treatment energy with the first treatment unit;
generating a second treatment energy with the second treatment unit;
wherein the second treatment energy is different than the first treatment energy;
providing the first treatment energy to the body part of the patient with the first treatment energy source to cause a treatment effect;
providing the second treatment energy to the body part of the patient with the second treatment energy source to cause the treatment effect; and
guiding the treatment with the control unit according to a selected one or more predefined treatment protocols in order to improve the visual appearance of the patient.

18. The method of claim 17, wherein the first treatment energy and the second treatment energy are selected from: a radio-frequency, a plasma, an ultrasound, acoustic waves, shock waves, a light, an electric current, a magnetic field, a positive or negative pressure, a heating or a cooling.

19. The method of claim 17, further including applying the first treatment energy and the second treatment energy to the body part of the patient simultaneously during the treatment.

20. The method of claim 17, further including coupling the first applicator to the body part of the patient with a flexible or partly elastic belt;
wherein the device is configured to be self-operated without needing intervention by professional medical staff after the treatment is set and begins.

21. The method of claim 17, further including providing a network communication between the device and an external device with one of: an optical cable, a conductive connection, a server or wireless transmission.

22. The method of claim 17, wherein the body part of the patient includes one of: a bra fat area, buttocks, saddlebags, love handles, an abdomen, hips, thighs, arms, a limb, a back, a cervical body part and also a muscle or muscle group of the mentioned body parts, which is treated in order to improve the visual appearance of the patient.

23. The method of claim 17, further including removably connecting a third treatment unit to the slot of the mother case by the user in a plug and play regime;
detecting the third treatment unit with a control unit;
connecting the first applicator to the third treatment unit by the user;
wherein the first applicator further comprises a third treatment energy source;
providing another predefined treatment protocol to the user based on a detection of the third treatment unit;
generating a third treatment energy with the third treatment unit,
wherein the third treatment energy is different from the first and second treatment energies; and
providing the third treatment energy to the body of the patient with the third treatment energy source in order to improve the visual appearance of the patient.

24. The method of claim 17, further including a second applicator comprising fourth and fifth treatment energy sources;
wherein the second applicator is connected to the first and second treatment units;
coupling the second applicator to the body part of the patient;
applying the first treatment energy to the body part of the patient with the fourth treatment energy source to cause the treatment effect; and
applying the second treatment energy to the body part of the patient with the fifth treatment energy source to cause the treatment effect.

25. A method of improving a visual appearance of a patient with a modular treatment device, comprising:
connecting a plurality of treatment units to a mother case via slots;
wherein the plurality of treatment units are removably plugged to the mother case;
detecting and configuring the plurality of treatment units in the mother case by a control unit,
wherein the control unit includes a processor and a memory;
wherein the control unit contains at least one predefined treatment protocol; and wherein the control unit is configured to control the plurality of treatment units;

connecting an applicator to the plurality of treatment units and coupling the applicator to a body part of the patient;

wherein the applicator includes at least one treatment energy source;

selecting the at least one predefined treatment protocol by the user of the modular treatment device;

generating treatment energies with the plurality of treatment units according to the selected at least one predefined treatment protocol, wherein each of the plurality of treatment units generates a different type of the treatment energy;

providing a plurality of treatment energies to the body part of the patient with the at least one treatment energy source; and guiding the treatment with the control unit in order to improve the visual appearance of the patient.

26. The method of claim 25, further including providing the plurality of energies to the body part of the patient simultaneously during one treatment;

wherein the plurality of energies are applied to the patient at the same time, sequentially or with an overlay.

27. The method of claim 25, further including coupling the applicator to the body part of the patient with a flexible or partly elastic belt;

wherein the device is configured to be self-operated.

28. The method of claim 25, wherein the device includes at least one sensor providing feedback information to the processor;

wherein the at least one sensor monitors device parameters, treatment parameters or biological, physical or chemical paramaters of the body part.

29. A method of a improving a visual appearance of a patient with a modular treatment device, comprising:

connecting a first treatment unit and a second treatment unit to a mother case;

wherein the mother case includes a control unit and slots;

wherein the first and second treatment units are connected to the slots of the mother case in a plug and play regime; and wherein the first and second treatment units are interconnected;

providing one or more predefined treatment protocols to the user, based on a detection of the first and second treatment units by the control unit, wherein the control unit includes a processor and a memory;

connecting an applicator to the first and second treatment units and coupling the applicator to a body part of the patient, wherein the applicator includes a plurality of first treatment energy sources and a plurality of second treatment energy sources;

generating a first treatment energy with the first treatment unit;

generating a second treatment energy with the second treatment unit;

wherein the second treatment energy is different than the first treatment energy;

providing a first treatment energy to the body part of the patient with the plurality of first treatment energy sources to cause a treatment effect;

providing a second treatment energy to the body part of the patient with the plurality of second treatment energy sources to cause the treatment effect; and guiding the treatment with the control unit in order to improve the visual appearance of the patient.

30. The method of claim 29, further comprising creating a treatment pattern by varying intensities of the first and second treatment energies between the plurality of first and second treatment energy sources.

* * * * *